United States Patent
Stevens et al.

(10) Patent No.: US 11,679,206 B2
(45) Date of Patent: Jun. 20, 2023

(54) SEMI-REUSABLE PALM ACTIVATED INJECTOR SYSTEM

(71) Applicant: West Pharmaceutical Services, Inc., Exton, PA (US)

(72) Inventors: Kevin Stevens, Mesa, AZ (US); Ian Scrimgeour, Leith Edinburgh (GB); Scott Salter, Leith Edinburgh (GB); Andrew Blair, Leith Edinburgh (GB); Alan Kitching, Leith Edinburgh (GB); David Sheperd, Leith Edinburgh (GB)

(73) Assignee: West Pharmaceutical Services, Inc., Exton, PA (US)

( * ) Notice: Subject to any disclaimer, the term of this patent is extended or adjusted under 35 U.S.C. 154(b) by 521 days.

(21) Appl. No.: 16/755,952

(22) PCT Filed: Oct. 22, 2018

(86) PCT No.: PCT/US2018/056955
§ 371 (c)(1),
(2) Date: Apr. 14, 2020

(87) PCT Pub. No.: WO2019/079828
PCT Pub. Date: Apr. 25, 2019

(65) Prior Publication Data
US 2020/0238014 A1    Jul. 30, 2020

Related U.S. Application Data

(60) Provisional application No. 62/574,973, filed on Oct. 20, 2017.

(51) Int. Cl.
*A61M 5/315* (2006.01)
*A61M 5/00* (2006.01)
*A61M 5/32* (2006.01)

(52) U.S. Cl.
CPC .......... *A61M 5/3157* (2013.01); *A61M 5/002* (2013.01); *A61M 5/3204* (2013.01);
(Continued)

(58) Field of Classification Search
CPC .. A61M 5/3157; A61M 5/002; A61M 5/3204; A61M 2205/18; A61M 2205/581; A61M 2205/584
(Continued)

(56) References Cited

U.S. PATENT DOCUMENTS 6,223,786 B1 * 5/2001 Castellano ............ A61J 1/2089
604/82
2013/0310759 A1    11/2013 Hourmand et al.
(Continued)

FOREIGN PATENT DOCUMENTS

CN    102665805 A    9/2012
CN    103108666 A    5/2013
(Continued)

OTHER PUBLICATIONS

Int'l Search Report and Written Opinion dated Jan. 11, 2019 in Int'l Application No. PCT/US2018/056955.
(Continued)

*Primary Examiner* — Phillip A Gray
(74) *Attorney, Agent, or Firm* — Blank Rome LLP

(57) ABSTRACT

An injection system includes a handle assembly with a handle body having an outer surface surrounding a handle body interior and a plunger extending therethrough. A tubular handle collar is telescopically received in the handle body exterior and is axially movable with respect to the handle body. A syringe housing assembly is selectively connectable to the handle assembly and includes a syringe housing and a tubular syringe sleeve telescopically received through a distal end of the syringe housing and axially
(Continued)

movable with respect thereto. The syringe housing has an exterior side surface surrounding a syringe housing interior configured to receive at least a portion of a syringe. The syringe sleeve has a proximal end, a distal end with a skin contact surface, and a generally cylindrically-shaped outer surface.

20 Claims, 27 Drawing Sheets

(52) U.S. Cl.
CPC ... *A61M 2205/18* (2013.01); *A61M 2205/581* (2013.01); *A61M 2205/584* (2013.01)

(58) Field of Classification Search
USPC ........................................................ 206/571
See application file for complete search history.

(56) References Cited

U.S. PATENT DOCUMENTS

| | | |
|---|---|---|
| 2014/0142507 A1 | 5/2014 | Armes |
| 2014/0324021 A1 | 10/2014 | Ulrich et al. |

FOREIGN PATENT DOCUMENTS

| | | |
|---|---|---|
| CN | 103732275 A | 4/2014 |
| CN | 103945879 A | 7/2014 |
| WO | 9906100 A2 | 2/1999 |
| WO | 2011047298 A2 | 4/2011 |

OTHER PUBLICATIONS

Int'l Preliminary Report on Patentability dated Jan. 7, 2020 in Int'l Application No. PCT/US2018/056955.

* cited by examiner

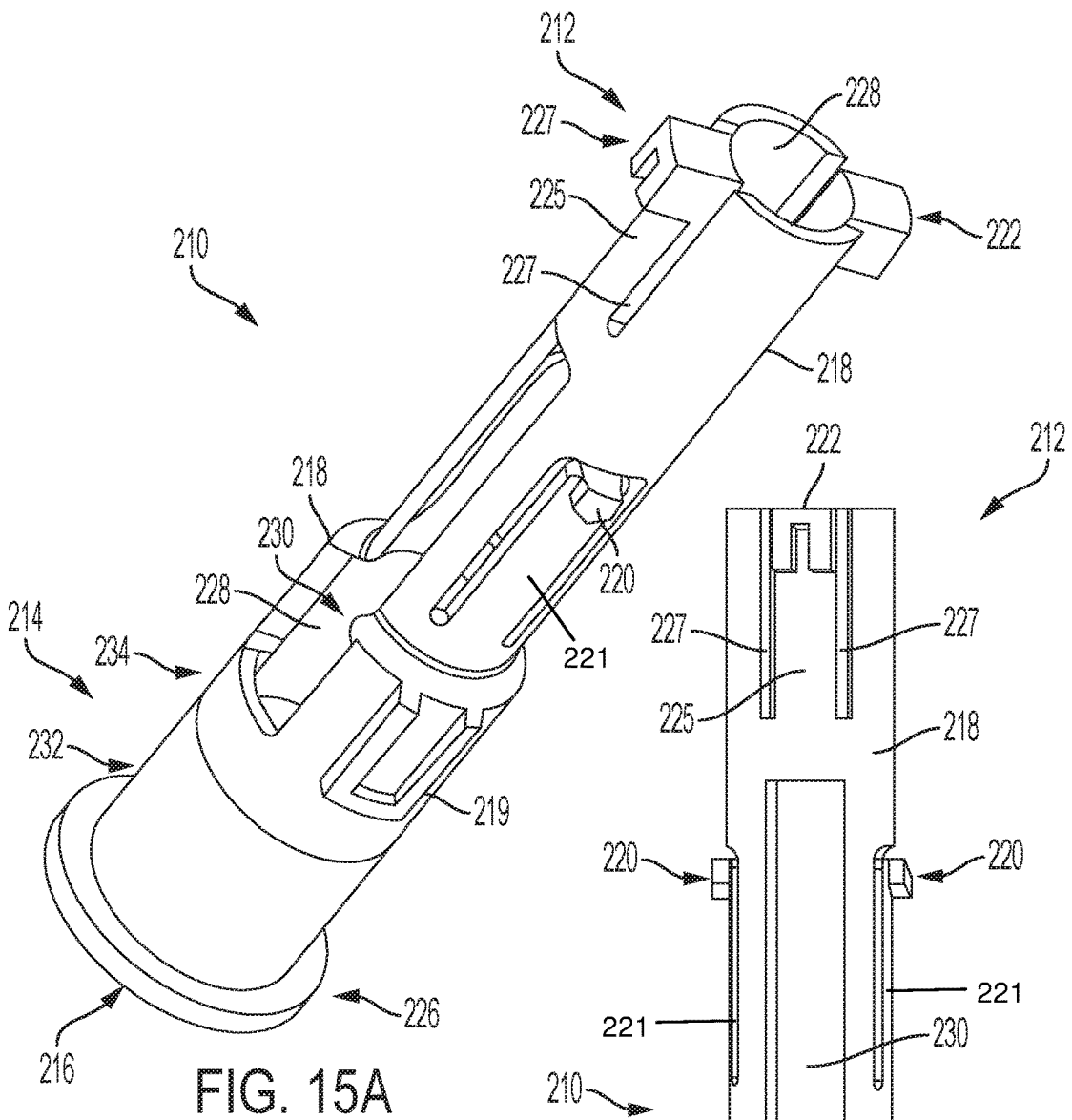
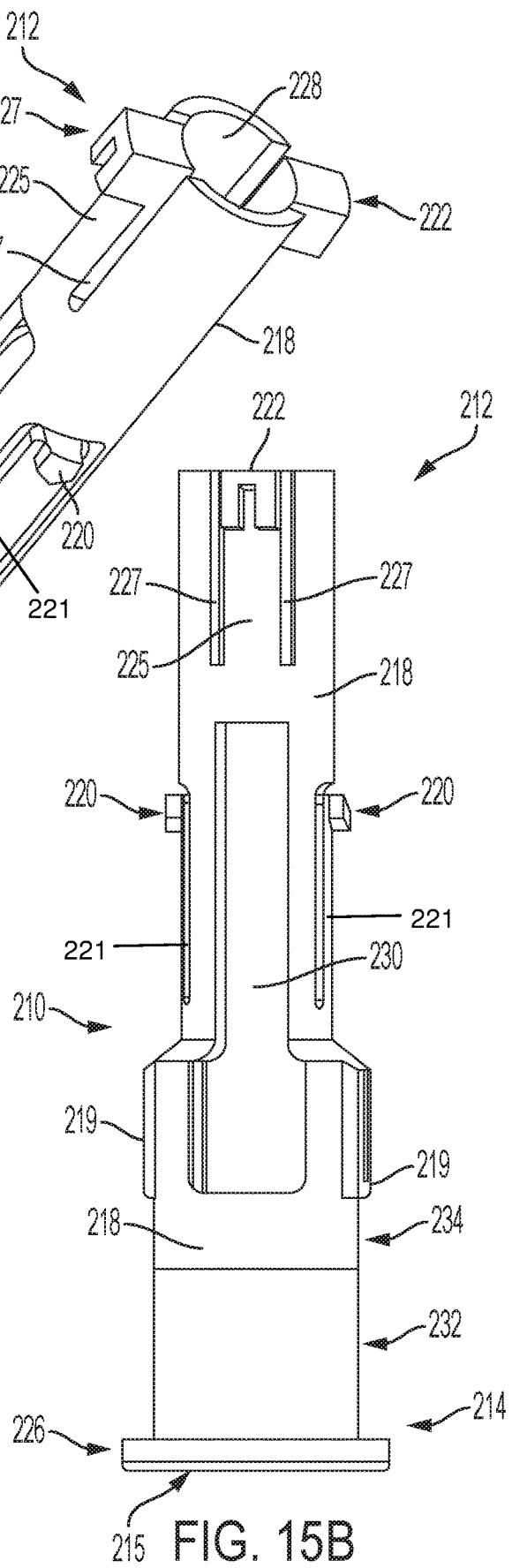
FIG. 15A
FIG. 15B

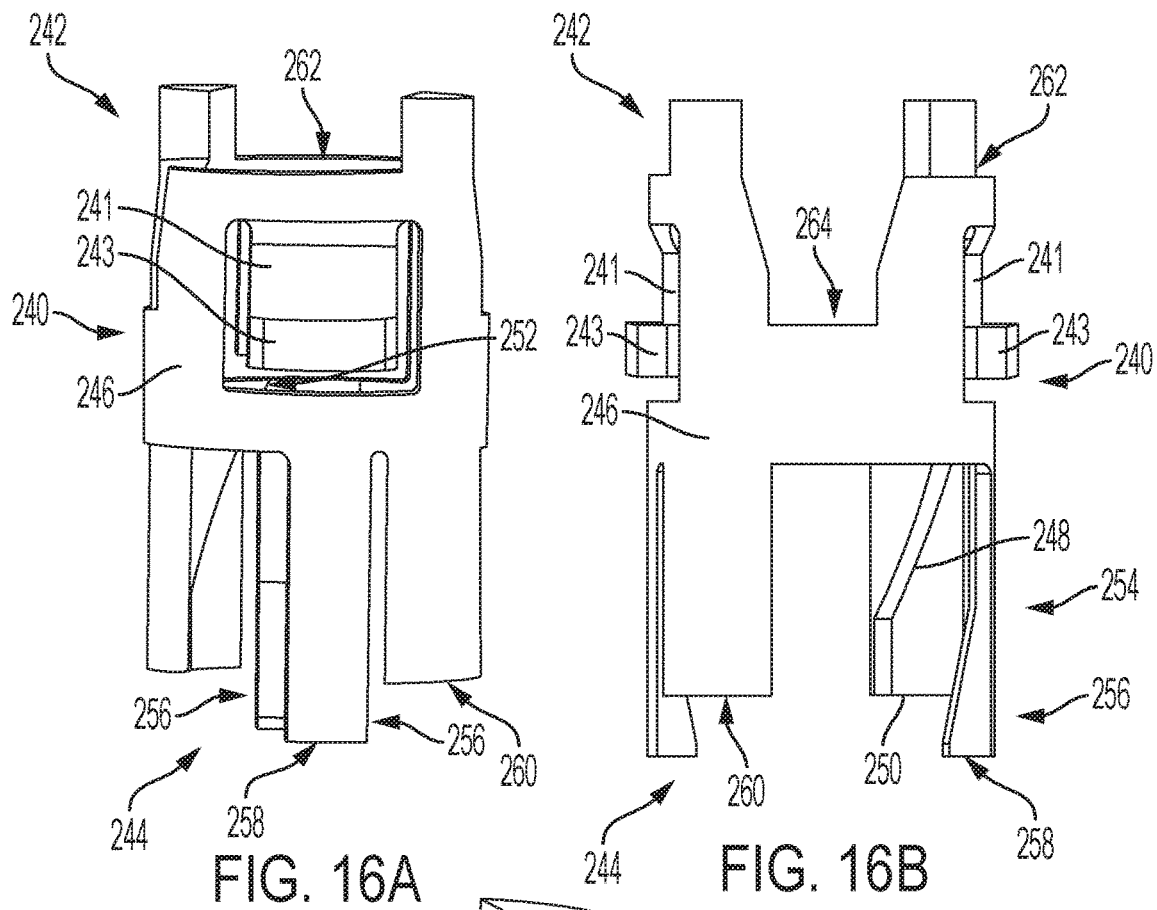
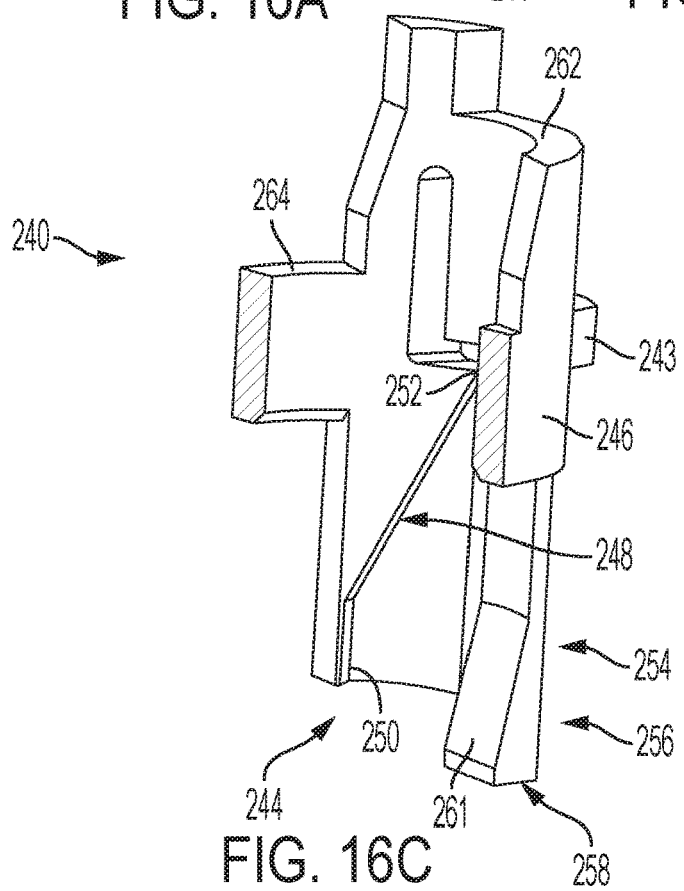
FIG. 16A
FIG. 16B
FIG. 16C

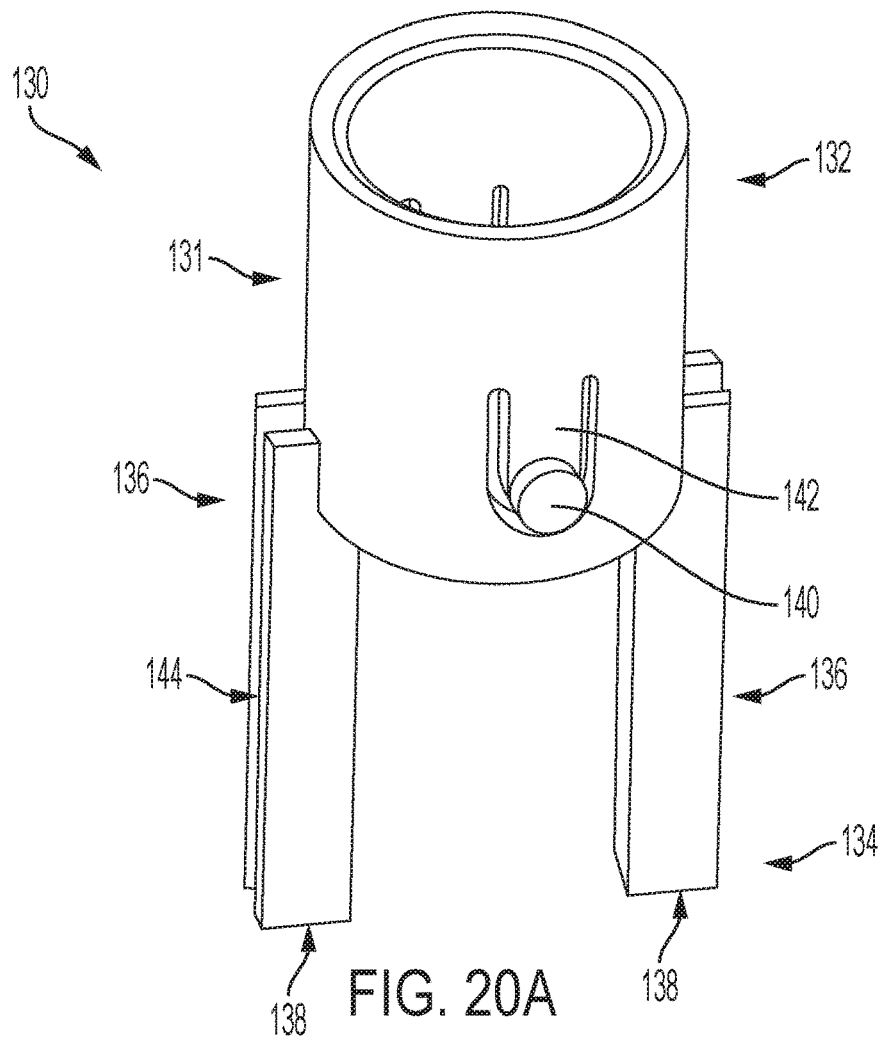
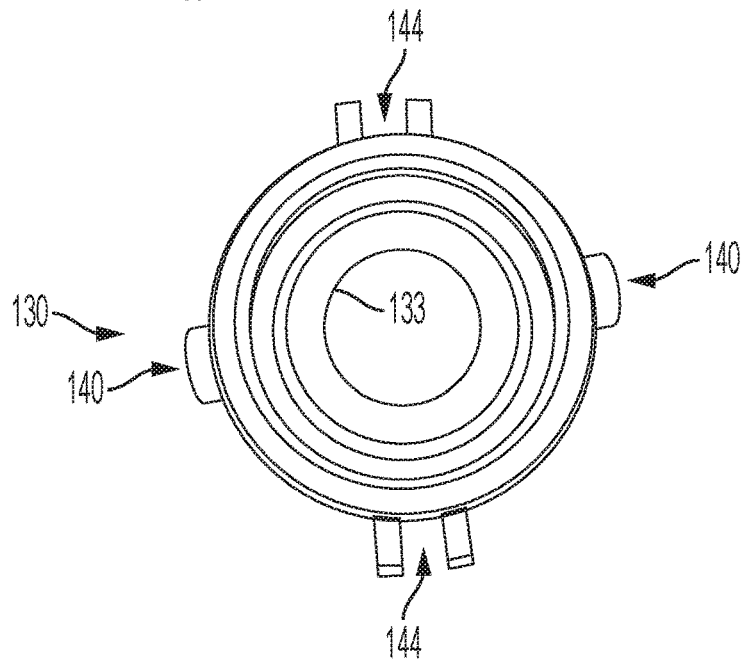
FIG. 20A
FIG. 20B

SEMI-REUSABLE PALM ACTIVATED INJECTOR SYSTEM

CROSS-REFERENCE TO RELATED APPLICATIONS

This application is a section 371 of International Application No. PCT/US2018/056955, filed Oct. 22, 2018, which was published on Apr. 25, 2019 under International Publication No. WO 2019/079828 A1, and which claims priority from U.S. Provisional Patent Application No. 62/574,973 filed on Oct. 20, 2017, the contents of each of which are incorporated herein by reference.

BACKGROUND

The present invention relates generally to the field of injection systems, and in particular to a system for aiding a user in injecting medicine by way of the needle of a syringe. In certain embodiments, the invention may aid the user in injecting medicine using a syringe with a needle, where the invention may allow the user to inject medicine with a reusable handle assembly connected to a disposable prefilled syringe assembly having built-in safeguards to minimize exposure to the needle. Embodiments of the invention may facilitate safe and simple connection and disconnection of the two assemblies before and after injection, providing the patient with an easy-to-use injection system and a reduced risk of injury through accidental needle sticks.

SUMMARY OF THE DISCLOSURE

Briefly stated, an example of an injection system comprises a handle assembly having a longitudinal axis, a proximal end, and a distal end. The handle assembly includes a handle body having a proximal end, a distal end, and an outer surface surrounding a handle body interior. A handle body opening is provided at the distal end of the handle body for accessing the handle body interior, and a plunger extends through the handle body interior. A tubular handle collar is telescopically received within the handle body interior through the handle body opening and movable along the longitudinal axis with respect to the handle body. The handle collar has a handle collar distal restraint limiting relative distal movement of the handle collar with respect to the handle body, and a longitudinally extending arm with a radially inwardly extending snap fitting disposed at a free end thereof. A syringe housing assembly is selectively connectable to the handle assembly and oriented to the longitudinal axis when connected to the handle assembly. The syringe housing assembly includes a syringe housing having a proximal end, a distal end, and an exterior side surface surrounding a syringe housing interior configured to receive at least a portion of a syringe. The exterior side surface has a syringe housing exterior snap fitting for selectively engaging the handle collar snap fitting when the handle assembly and the syringe housing assembly are connected. A tubular syringe sleeve is telescopically received within the syringe housing interior through a distal end of the syringe housing and is axially movable with respect to the syringe housing. The syringe sleeve has a proximal end, a distal end with a skin contact surface, and a generally cylindrically-shaped outer surface.

Another example of an injection system includes a handle assembly having a longitudinal axis, a proximal end, and a distal end. The handle assembly includes a handle body having a proximal end, a distal end, a plunger extending parallel to the longitudinal axis. A tubular handle collar is telescopically received within the handle body interior through the handle body opening and movable along the longitudinal axis with respect to the handle body. The handle collar has a longitudinally extending arm with a radially inwardly extending snap fitting disposed at a free end thereof. A handle bias member is disposed between the handle body and the handle collar along the longitudinal axis. A syringe housing assembly is selectively connectable to the handle assembly and oriented to the longitudinal axis when connected to the handle assembly. The syringe housing assembly includes a syringe housing having a proximal end, a distal end, and a syringe housing exterior snap fitting for selectively engaging the handle collar snap fitting when the handle assembly and the syringe housing assembly are connected. The syringe housing is configured to receive and support a syringe. A tubular syringe sleeve is telescopically received within the syringe housing and is axially movable with respect to the syringe housing. The syringe sleeve has a proximal end and a distal end with a skin contact surface. The syringe sleeve has a first syringe sleeve position wherein the distal end of the syringe sleeve is axially separated from the distal end of the syringe housing by a first distance, a second syringe sleeve position wherein the distal end of the syringe sleeve is axially separated from the distal end of the syringe housing by a second distance that is smaller than the first distance, and a third syringe sleeve position wherein the distal end of the syringe sleeve is axially separated from the distal end of the syringe housing by a third distance that is larger than the first distance. The handle bias member biases the syringe sleeve toward the third syringe sleeve position when the handle assembly is connected to the syringe housing assembly. The injection system has a first configuration wherein the handle assembly is disconnected from the syringe housing assembly and the syringe sleeve is in the first syringe sleeve position, a second configuration wherein the handle assembly is connected to the syringe housing assembly and the syringe sleeve is in the first syringe sleeve position, a third configuration wherein the handle assembly is connected to the syringe housing assembly and the syringe sleeve is in the second syringe sleeve position, a fourth configuration wherein the handle assembly is connected to the syringe housing assembly and the syringe sleeve is in the third syringe sleeve position, and a fifth configuration wherein the handle assembly is disconnected from the syringe housing assembly and the syringe sleeve is in the third syringe sleeve position.

Another example of an injection system includes a tray having a plurality of storage tubes and a handle storage tube. Aa handle assembly is stored in the handle storage tube. The handle assembly has a longitudinal axis, a proximal end, and a distal end. The handle assembly includes a handle body having a proximal end, a distal end, and an outer surface surrounding a handle body interior. A handle body opening is provided at the distal end of the handle body for accessing the handle body interior, and a plunger extends through the handle body interior and is oriented parallel to the longitudinal axis. A tubular handle collar is telescopically received within the handle body interior through the handle body opening and movable along the longitudinal axis with respect to the handle body. The handle collar has a handle collar distal restraint limiting relative distal movement of the handle collar with respect to the handle body, and a longitudinally extending arm with a radially inwardly extending snap fitting disposed at a free end thereof. A syringe housing assembly is selectively connectable to the handle assembly and oriented to the longitudinal axis when connected to the handle assembly. A plurality of syringe housing assemblies is included, each syringe housing assembly being stored in a corresponding one of the plurality of storage tubes and being selectively connectable to the handle assembly and oriented to the longitudinal axis when connected to the handle assembly. Each syringe housing assembly includes a syringe housing having a proximal end, a distal end, and an exterior side surface surrounding a syringe housing interior configured to receive at least a portion of a syringe. The exterior side surface has a syringe housing exterior snap fitting for selectively engaging the handle collar snap fitting when the handle assembly and the syringe housing assembly are connected. A tubular syringe sleeve is telescopically received within the syringe housing interior through a distal end of the syringe housing and is axially movable with respect to the syringe housing. The syringe sleeve has a proximal end, a distal end with a skin contact surface, and a generally cylindrically-shaped outer surface.

In certain embodiments, the tubular handle collar is rotatably fixed with respect to the handle body.

In certain embodiments, the handle assembly further includes a handle bias member disposed between the handle body and the handle collar along the longitudinal axis to urge the handle body in a proximal direction away from the handle collar.

In certain embodiments, the syringe sleeve has a first syringe sleeve position wherein the distal end of the syringe sleeve is axially separated from the distal end of the syringe housing by a first distance, a second syringe sleeve position wherein the distal end of the syringe sleeve is axially separated from the distal end of the syringe housing by a second distance that is smaller than the first distance, and a third syringe sleeve position wherein the distal end of the syringe sleeve is axially separated from the distal end of the syringe housing by a third distance that is larger than the first distance. The handle bias member biases the syringe sleeve toward the third syringe sleeve position when the handle assembly is connected to the syringe housing assembly.

In certain embodiments, a handle barrel is rotatably mounted and axially fixed with respect to the handle collar and has a generally cylindrical sidewall extending between proximal and distal ends of the handle barrel. A handle body landing extends radially from the sidewall. The handle barrel is rotatable with respect to the handle body between a first handle barrel position wherein the handle body landing is circumferentially aligned with and engages a radially extending handle body projection of the handle body to restrain a distal relative movement of the handle body with respect to the handle collar, and a second handle barrel position wherein the handle body landing is out of circumferential alignment with the handle body projection such that the handle body is free to move distally with respect to the handle collar. The handle barrel has a handle barrel track arranged on the sidewall of the handle barrel. The handle barrel track is oriented at least partially non parallel to the longitudinal axis between a first end and a second end of the handle barrel track.

In certain embodiments, a handle pusher is included having a proximal end and a distal end and a handle pusher lug at the distal end thereof, the handle pusher being telescopically received within the handle collar and rotatably fixed with respect to the handle collar. The handle pusher lug has a distal contact surface, and the handle pusher has a radially extending handle pusher projection that extends into the handle barrel track and is movable between the first and second ends of the handle barrel track such that, upon a proximal relative movement of the handle pusher with respect to the handle collar, the handle barrel rotates with respect to the handle collar from the first handle barrel position to the second handle barrel position, and upon a distal relative movement of the handle pusher with respect to the handle collar, the handle barrel rotates with respect to the handle collar from the second barrel handle position to the first barrel handle position.

In certain embodiments, the syringe sleeve has a locking pin extending radially outwardly from the syringe sleeve outer surface. The syringe sleeve has a radially outwardly extending syringe sleeve lug at a proximal end of the syringe sleeve; and the syringe housing has a lug landing selectively aligned with and configured to support the syringe sleeve lug.

In certain embodiments, a rotary collar is included, the rotary collar being rotatably mounted and axially fixed within the syringe housing interior, the rotary collar having a proximal end, a distal end, a generally cylindrical sidewall, and a cam surface formed in the sidewall of the rotary collar. At least a portion of the cam surface extends from a first cam end proximate the distal end of the rotary collar to a second cam end that is spaced apart proximally and circumferentially from the first cam end. The rotary collar further includes a flexible locking arm extending axially toward a free end with a distally facing locking surface that is distally located from the distal surface of the rotary collar. The locking pin is in contact with the cam surface at the first cam end when the syringe sleeve is in the first syringe sleeve position such that, upon proximal movement of the syringe sleeve with respect to the syringe housing from the first syringe sleeve position to the second syringe sleeve position, the locking pin interacts with the cam surface to rotate the rotary collar with respect to the syringe housing from a first rotary collar position to a second rotary collar position wherein the locking pin ceases contact with the cam surface at the second cam end and is circumferentially aligned with the locking arm and the syringe sleeve is in the second syringe sleeve position. Upon subsequent distal movement of the syringe sleeve with respect to the syringe housing to the third syringe sleeve position, the locking pin moves distally with respect to the rotary collar along the locking arm until the locking pin passes the locking surface of the locking arm. The locking surface prevents the locking pin from moving proximally with respect to the rotary collar.

In certain embodiments, the rotary collar is in the first rotary collar position when the syringe sleeve is in the first syringe sleeve position, and the second rotary collar position when the syringe sleeve is in the second and third syringe sleeve positions. The rotary collar has a first proximally facing syringe sleeve contact surface and a second proximally facing syringe sleeve contact surface. The first syringe sleeve contact surface is in contact with a distally facing surface of the syringe sleeve lug when the rotary collar is in the first rotary collar position and the syringe sleeve is in the first syringe sleeve position to prevent distal movement of the syringe sleeve with respect to the syringe housing. The second syringe sleeve contact surface is in contact with the distally facing surface of the syringe sleeve lug when the rotary collar is in the second position and the syringe sleeve is in the third syringe sleeve position to prevent distal movement of the syringe sleeve with respect to the syringe housing.

In certain embodiments, the distal end of the syringe sleeve has a radially outwardly extending annular locking flange, and the injection system further includes a storage tube. The storage tube includes a storage tube body having a proximal end, a distal end, a side wall, a cavity accessible through an opening at the proximal end of the storage tube body for accepting the syringe housing assembly, a syringe housing assembly landing within the cavity for supporting the syringe housing assembly, and a syringe housing assembly lock positioned within the cavity such that when the syringe housing assembly is supported by the syringe housing assembly landing and the syringe sleeve is in the first syringe sleeve position, the syringe housing assembly lock does not engage the locking ring of the syringe sleeve, and when the syringe housing assembly is supported by the syringe housing assembly landing and the syringe sleeve is in the third syringe sleeve position, the syringe housing assembly lock engages the locking ring of the syringe sleeve and locks the syringe housing assembly within the storage tube. A distance between the proximal end of the storage tube and the syringe housing assembly lock is sufficient that the proximal end of the syringe housing assembly is countersunk distally from the proximal end of the storage tube.

In certain embodiments, an audio alert means is configured to provide an audio alert when the handle body reaches an end of injection position such that the handle body cannot move any further distally with respect to the handle collar.

In certain embodiments, the audio alert means comprises a striker, a strike plate, an alert biasing member operatively connected to the striker, and a striker pusher for biasing the striker with respect to the strike plate and releasing the striker to strike the strike plate upon the handle body reaching the end of injection position.

In certain embodiments, the striker pusher comprises a track engaging at least one of the alert biasing member and the striker during movement of the handle body with respect to the handle collar and releasing the striker upon the handle body reaching the end of injection position, the biasing member is attached to the handle collar, and the striker is attached to an end portion of the biasing member.

In certain embodiments, the injection system includes a tray comprising a plurality of storage tubes.

In certain embodiments, a handle storage tube is attached to the tray. The handle storage tube has a handle cavity for accepting the handle assembly. The handle storage tube includes a handle storage tube snap, and the outer surface of the handle body includes a flexible storage arm carrying a snap for engaging the handle storage tube snap of the handle storage tube to secure the handle assembly in the handle storage tube.

In certain embodiments, the injection system includes a cap for the storage tube.

BRIEF DESCRIPTION OF THE SEVERAL VIEWS OF THE DRAWINGS

The foregoing summary, as well as the following detailed description of examples of systems and devices according to the invention, will be better understood when read in conjunction with the appended drawings. For the purpose of illustrating the invention, there are shown in the drawings embodiments which are presently preferred. It should be understood, however, that the disclosure is not limited to the precise arrangements and instrumentalities shown. In the drawings:

FIGS. 15A and 15B are perspective and left side elevational views of a syringe sleeve for use in the system of FIG. 1

FIGS. 16A and 16B are perspective and left side elevational views of a rotary collar for use in the system of FIG. 1;

FIG. 16C is a cutaway view of the rotary collar of FIG. 16A;

FIG. 20A is a perspective view of a handle pusher for use in the system of FIG. 1; and FIG. 20B is a top plan view of the handle pusher of FIG. 20A.

DETAILED DESCRIPTION

Figure 1:
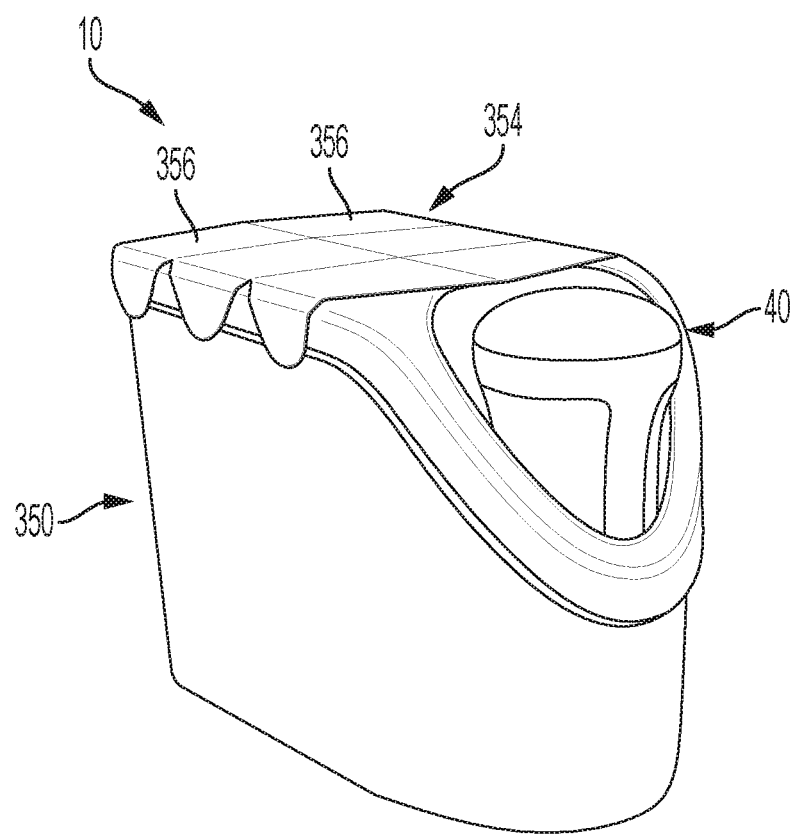
FIG. 1 is a left front perspective view of an embodiment of an injection system according to the invention.

Certain terminology is used in the following description for convenience only and is not limiting. The words "lower," "bottom," "upper," "top," "front," "back," and "rear" designate directions in the drawings to which reference is made. The words "inwardly" and "outwardly" refer to directions toward and away from, respectively, the geometric center of the component being discussed, and designated parts thereof, in accordance with the present disclosure. Unless specifically set forth herein, the terms "a," "an," and "the" are not limited to one element, but instead should be read as meaning "at least one." "At least one" may occasionally be used for clarity or readability, but such use is not change the interpretation of "a," "an," and "the." The terminology includes the words noted above, derivatives thereof, and words of similar import Moreover, the singular includes the plural, and vice versa, unless the context clearly indicates otherwise. Various components are described in terms of a single component; however, the illustrated embodiment, or other embodiments not illustrated, may include two or more of the same component, as illustrated in the drawings or noted in the specification, or as otherwise would be understood by a person of skill in the art. Various components are described as being secured against movement or flexing; these references do not contemplate the absolute elimination of all movement or flexing. Instead, these references include restriction or movement of flexing sufficient to alter the functionality of the component or components in operative relation therewith. References to a component extending, moving, or flexing in a particular direction refer to the component extending, moving, or flexing at least partially in the particular direction; an extension, movement, or flexion that includes any component of movement in the particular direction is included.

Figure 18A:
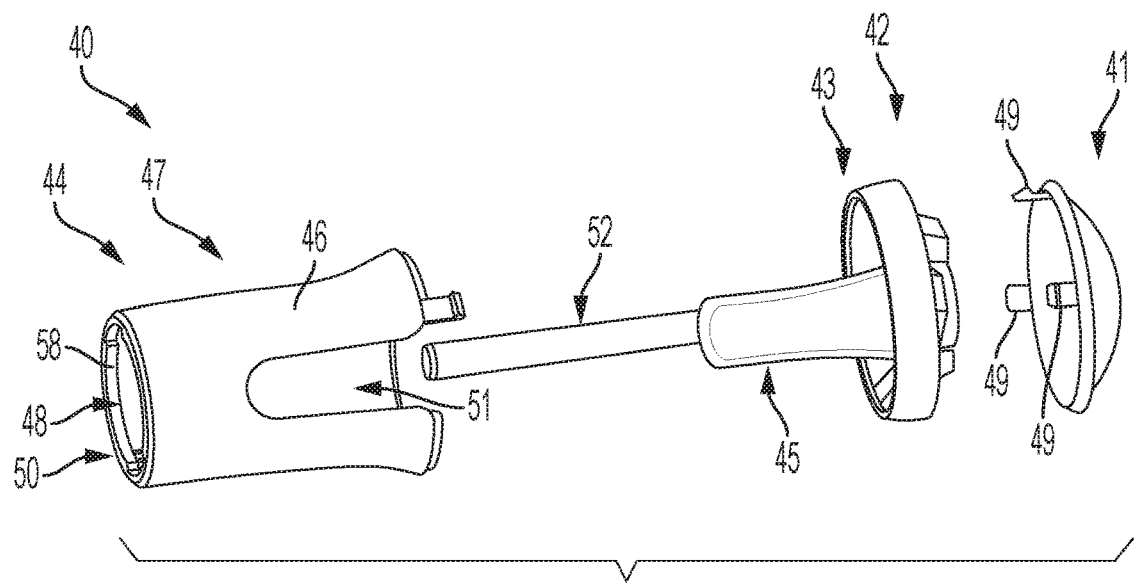
FIG. 18A is an exploded partial perspective view of a handle body for use in the system of FIG. 1.
Figures 18B, 18C:
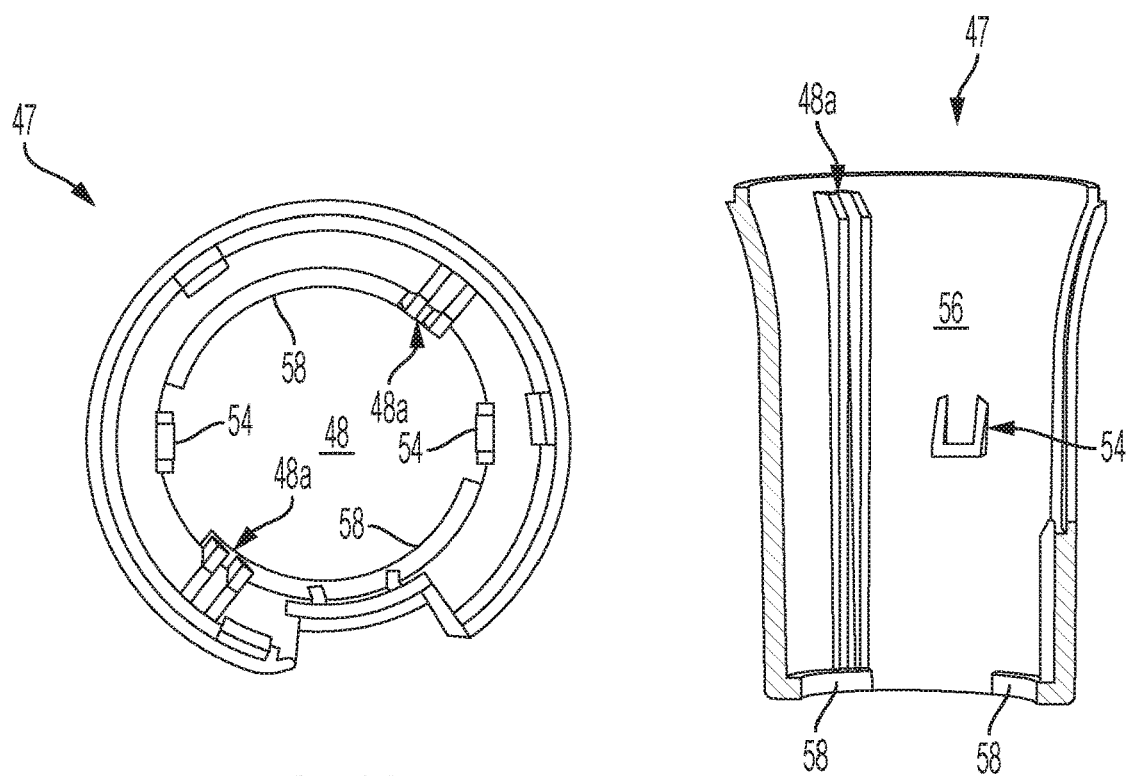
FIGS. 18B and 18C are sectional views of the handle sleeve of FIG. 18A.

Referring to FIGS. 8A through 13B, an example of an injection system 10 includes a handle assembly 20 and a syringe housing assembly 160. The handle assembly 20 has a longitudinal axis 22, a proximal end 24, and a distal end 26. The handle assembly 20 includes a handle body 40 having a proximal end 42, a distal end 44, and an outer surface 46 surrounding a handle body interior 48. A handle body opening 50 is provided at the distal end 44 of the handle body 40 for accessing the handle body interior 48, and a plunger 52 extends through the handle body interior 48 and is oriented parallel to the longitudinal axis 22. Referring to FIG. 18A, the handle body 40 includes a handle cap 41, which attaches to a handle ring 43 via distally extending connector snap fittings 49. The plunger 52 is preferably connected to the handle ring 43, and may be integrally formed therewith. The handle ring 43 preferably also includes at least one distally extending main handle tab 45. The handle ring 43 preferably attaches coaxially to a handle sleeve 47 via a proximally extending connector tab 46a, with the main handle tab 45 fitting into a correspondingly shaped main handle slot 51, which stabilizes the handle ring 43 with respect to the handle sleeve 47. The handle body 40 has a distal restraint in the form of a distal flange 58 (FIGS. 18B, 18C), which will be explained in further detail below. The handle body 40 has a pair of handle body projections 54, which in the embodiment shown extend radially inwardly, and which interact with a handle barrel 100 (FIGS. 19A through 19C) to lock the handle 40 in the manner discussed below.

Although the handle body 40 is shown in the present embodiment to have an essentially three-piece construction, the handle body 40 is not limited to such a configuration and can be formed from more or fewer components without departing from the concept of the present invention. For example, the handle cap 41 and the handle ring 43 may be integrally formed as one piece. In another example, the plunger 52 may be coupled to the handle ring 43 via a threaded connection. Other examples for the handle body 40 construction within the scope of the present invention will be apparent to those of ordinary skill in the art.

Figure 18D:
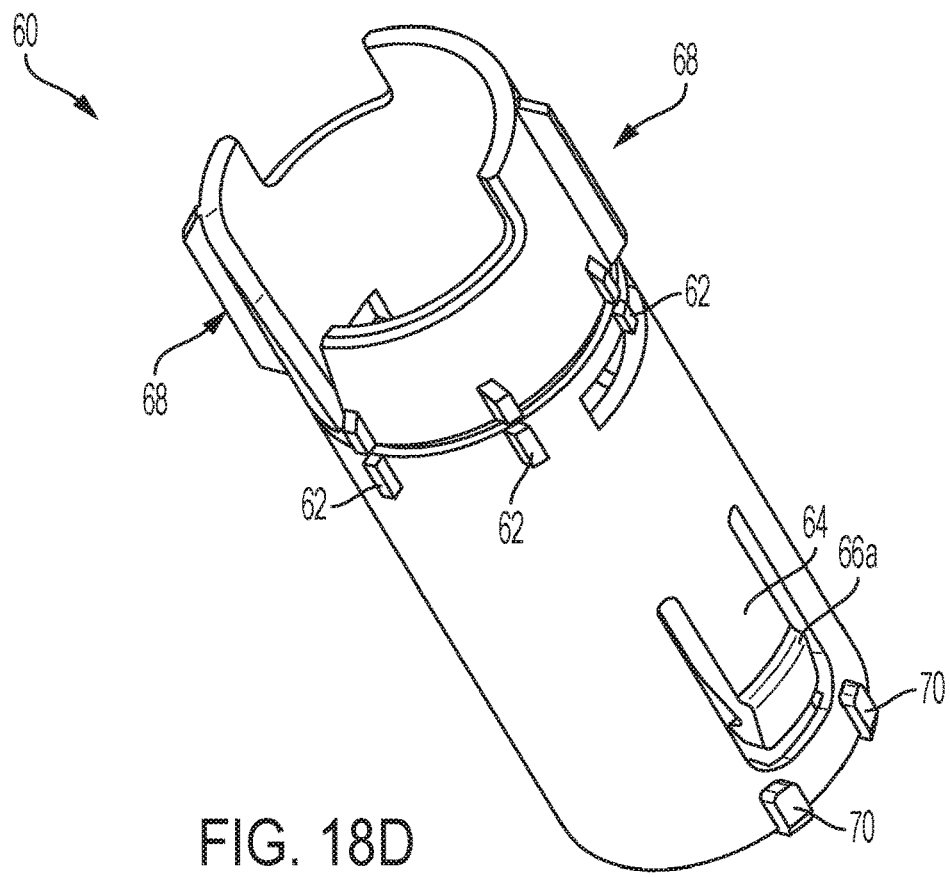
FIG. 18D is a perspective view of a handle collar for use in the system of FIG. 1.
Figure 18E:
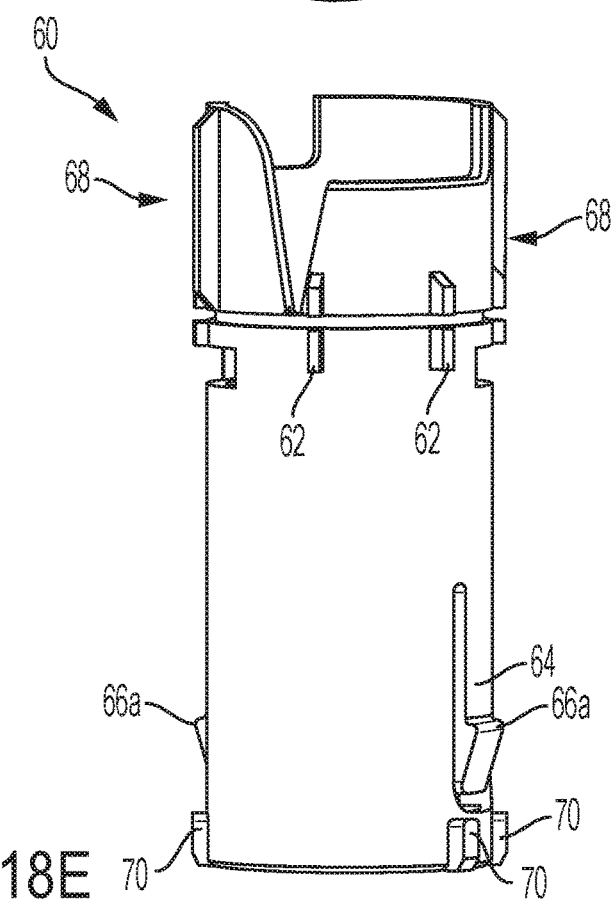
FIG. 18E is a front right elevational view of the handle body of FIG. 18A.

A tubular handle collar 60 is preferably telescopically received within the handle body interior 48 through the handle body opening 50 and is movable along the longitudinal axis 22 with respect to the handle body 40. The handle collar 60 preferably has a handle collar distal restraint in the form of a lug 62 limiting relative distal movement (FIGS. 18D, 18E) of the handle collar 60 with respect to the handle body 40, and a longitudinally extending arm 64 with a radially outwardly extending exterior snap fitting 66a and a radially inwardly extending interior snap fitting 66b disposed at a proximally located free end thereof. The handle collar 60 is rotatably fixed with respect to the handle body 40 by, for example, a pair of radially outwardly extending external projections 68 of the handle collar 60, each of which rides in a corresponding longitudinally extending internal track 56a disposed on an interior surface 56 of the handle body 40.

As may be seen in the sectional views, FIGS. 9B, 10B, 11B, 12B, and 13B, a handle bias member, here a coil spring 150, is disposed between the handle body 40 and the handle collar 60 along the longitudinal axis 22 to urge the handle body 40 in a proximal direction away from the handle collar 60. The spring 150 thus provides a force tending to extend the handle collar 60 outwardly from the handle body 40, so that the handle assembly 20 is biased toward axial extension.

Figure 9A:
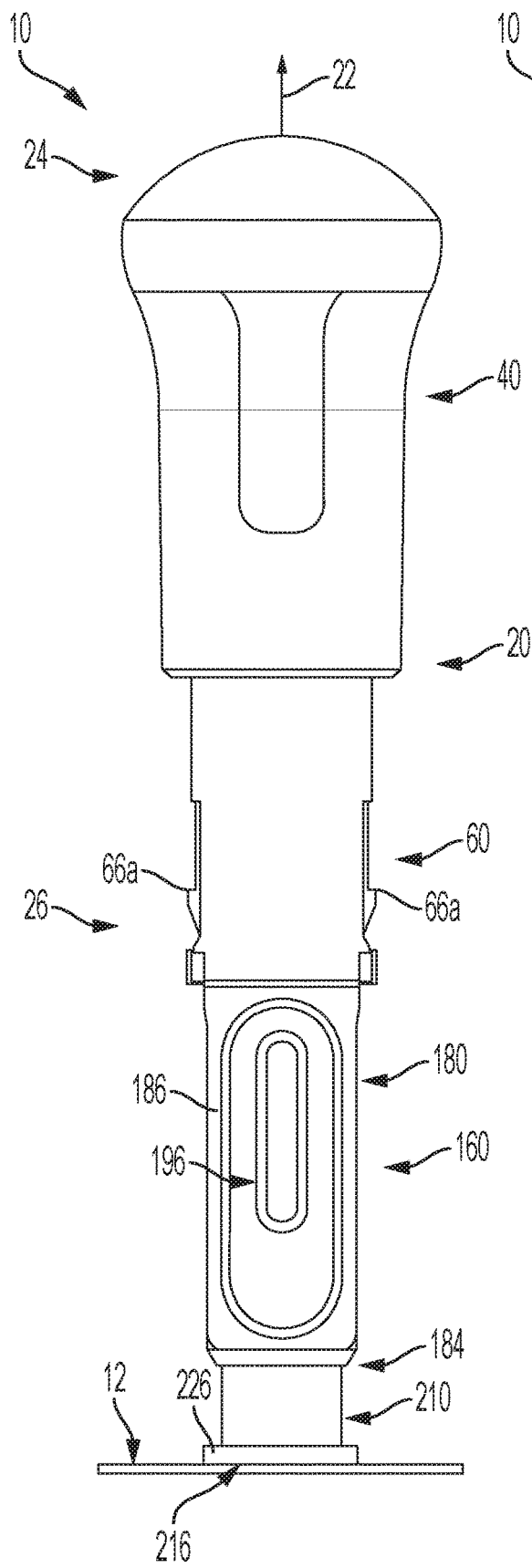
FIGS. 9A and 9B are front elevational and sectional views of the handle assembly and syringe housing assembly from the system of FIG. 1 in contact with a skin surface, with a syringe sleeve in the first position, prior to beginning an injection.
Figure 9B:
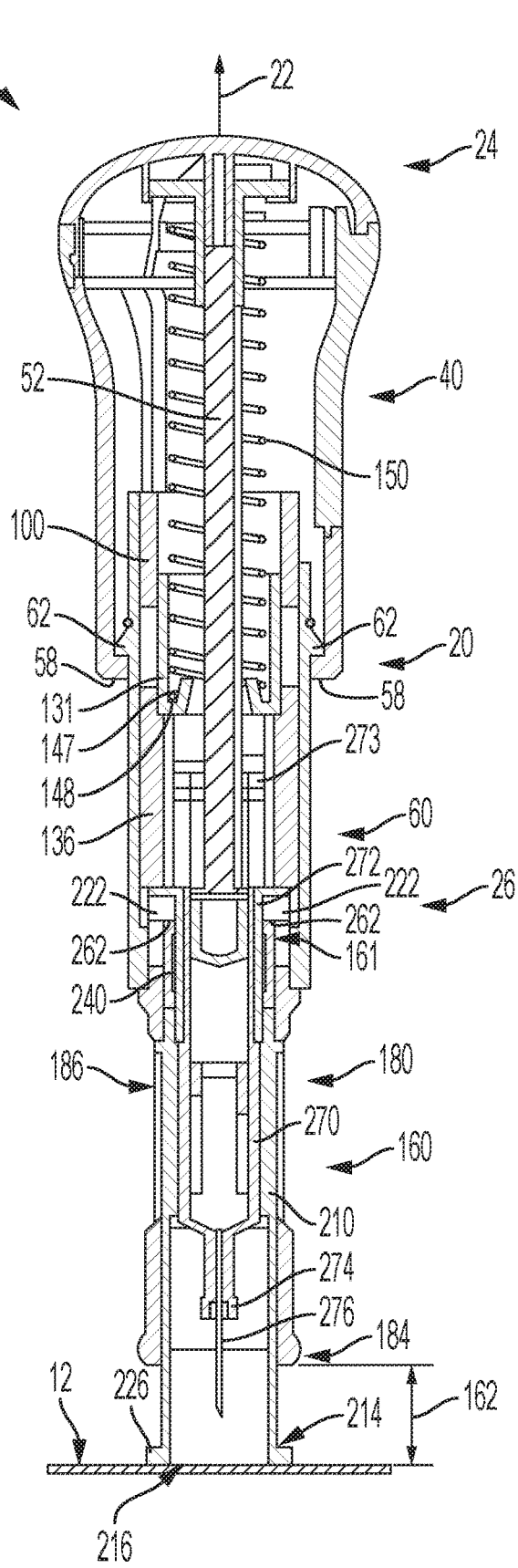
Figure 17A:
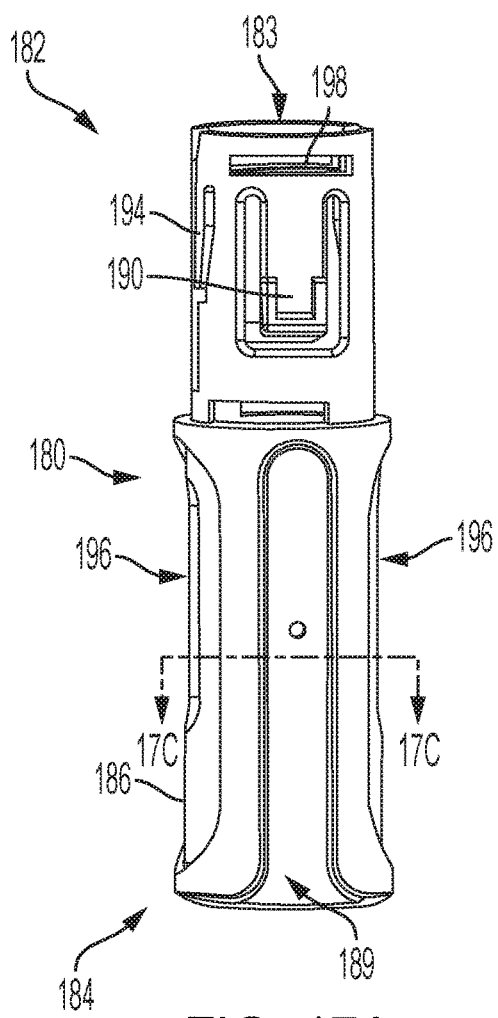
FIGS. 17A and 17B are perspective and left side elevational views of the syringe housing of FIG. 8A.
Figure 17B:
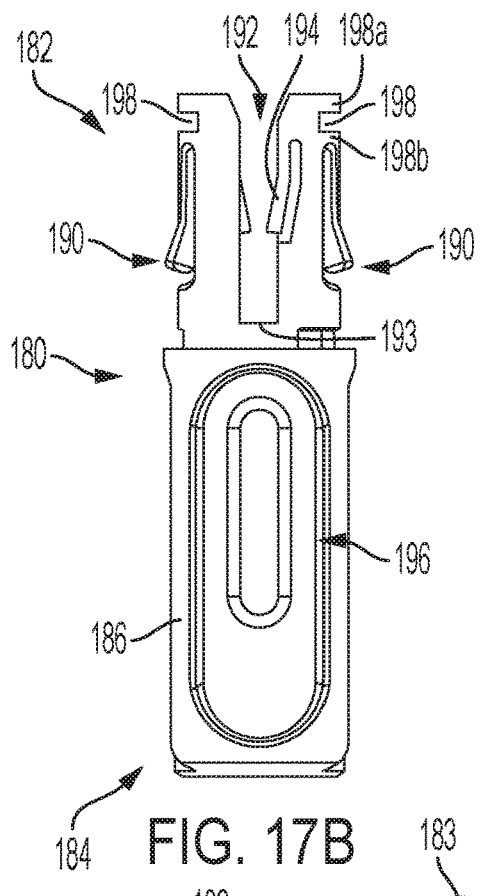
Figure 17C:
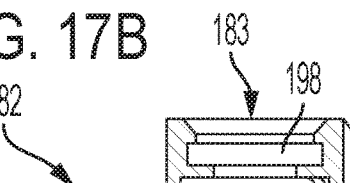
FIGS. 17C and 17D are sectional views of the syringe housing of FIG. 17A.
Figure 17D:
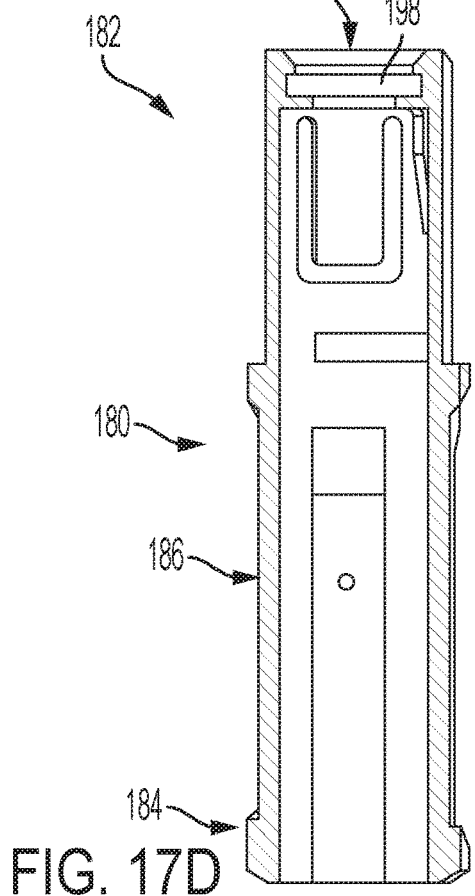

Referring to FIGS. 9B, 17A, and 17B, the syringe housing assembly 160 is selectively connectable to the handle assembly 20 and oriented to the longitudinal axis 22 when connected to the handle assembly 20. The syringe housing assembly 160 preferably includes a syringe housing 180 having a proximal end 182 with a proximal opening 183, a distal end 184, and an exterior side surface 186 surrounding a syringe housing interior 188 configured to receive at least a portion of a syringe 270. The syringe housing 180 has an exterior alignment track 189, which aligns with corresponding features of the handle collar 60, in this case the handle body projection 54, to maintain the syringe housing 180 in alignment with the handle collar 60. The exterior alignment track 190 may also interact with corresponding features of the storage tube 440 to maintain the syringe housing 180 in alignment with the storage tube 440. The syringe 270 may be a prefilled syringe having a proximal end 272, a proximal flange 273, and a distal end 274, and may have a needle 276 with a needle tip 278. The syringe 270 may have a removable needle shield 280 attached to the distal end 274 of the syringe 270. When placed within the syringe housing 180, the syringe 270 may be oriented to the longitudinal axis 22 and may receive the plunger 52 through the proximal end 272 of the prefilled syringe 270 when the handle assembly 20 is connected to the syringe housing assembly 160. The syringe housing 180 may have a distally located flange slot 198 with a proximal side 198a and a distal side 198b, the flange slot 198 engaging the proximal flange 273 to secure the syringe 270 in the syringe housing 180. The exterior side surface 186 of the syringe housing 180 preferably has a syringe housing exterior snap fitting 190 (FIG. 8E) for selectively engaging the exterior snap fitting 66a when the handle assembly 20 and the syringe housing assembly 160 are connected.

Referring now to FIGS. 15A and 15B, as well as FIGS. 8A through 13B, a tubular syringe sleeve 210 is telescopically received within the syringe housing interior 188 through a distal end 184 of the syringe housing 180 and is axially movable with respect to the syringe housing 180. The syringe sleeve 210 has a proximal end 212, a distal end 214 with a skin contact surface 216, and a generally cylindrically-shaped outer surface 218 configured to surround at least a portion of the syringe 270 contained in the syringe housing 180.

The syringe sleeve 210 has a first syringe sleeve position (FIGS. 9A and 9B) wherein the distal end 214 of the syringe sleeve 210 is axially separated from the distal end 184 of the syringe housing 180 by a first distance 162. The first syringe sleeve position preferably corresponds to an initial, pre-injection state, wherein the distal end 214 of the syringe sleeve 210 covers the needle tip 278. As will be described in further detail below, certain actions taken by the user to initiate injection are required in order to change the syringe sleeve 210 from this first position. The syringe sleeve 210 also has a second syringe sleeve position (FIGS. 10A through 11B) wherein the distal end 214 of the syringe sleeve 210 is axially separated from the distal end 184 of the syringe housing 180 by a second distance 164 that is smaller than the first distance 162 and may be a distance of zero because the distal end 214 of the syringe sleeve 210 is touching the distal end 184 of the syringe housing 180. The second syringe sleeve position preferably corresponds to a state during injection, where the needle tip 278 is embedded in the skin of the patient so that medicine in the syringe 270 can be administered. and the syringe sleeve 210 also has a third syringe sleeve position (FIGS. 12A and 12B) wherein the distal end 214 of the syringe sleeve 210 is axially separated from the distal end 184 of the syringe housing 180 by a third distance 166 that is larger than the first distance 162. The third syringe sleeve position preferably corresponds to a post-injection state, wherein the distal end 214 of the syringe sleeve 210 once again covers the needle tip 278 following removal of the syringe 270 from the skin surface. The third distance 166 preferably corresponds to current safety requirements for spacing the needle tip 278 at a sufficient distance such that the tip 278 cannot be reasonably accessed by the user's finger following injection. As explained in further detail below, the syringe sleeve 210 locks in position axially with respect to the syringe housing 180 to prevent reuse of the syringe 270. The syringe sleeve 210 has a guide projection 219 for aligning with a corresponding feature of the syringe housing 180 and maintaining the syringe sleeve 210 in alignment with the syringe housing 180.

The handle bias member, e.g., the spring 150, biases the syringe sleeve 210 toward the third syringe sleeve position when the handle assembly 20 is connected to the syringe housing assembly 160, as will be explained in further detail below. The syringe sleeve 210 may have a locking pin 220 carried on a proximally extending arm 221 and extending radially outwardly from the syringe sleeve outer surface 218 and may have a radially outwardly extending syringe sleeve lug 222 at a free end of a distally extending flexible arm 225 defined by two slots 227 at the proximal end 212 of the syringe sleeve 210. The distal end 214 of the syringe sleeve 210 may have a radially outwardly extending annular locking flange 226.

Figure 8A:
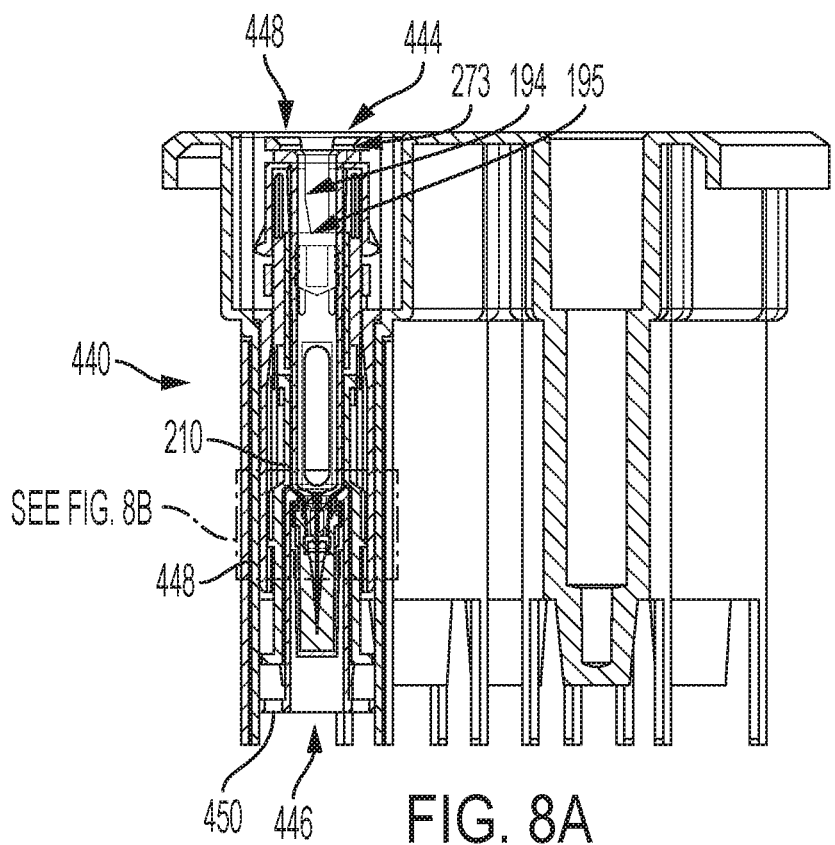
FIG. 8A is a left side sectional view of the system of FIG. 1.
Figure 8B:
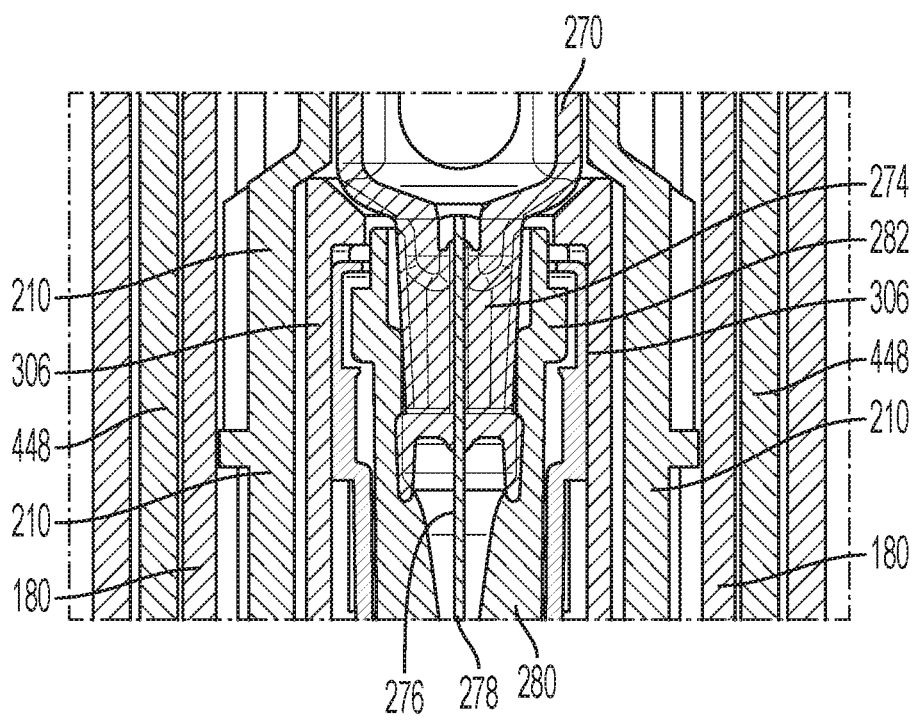
FIG. 8B is a magnified portion of the sectional view of FIG. 8A.

The syringe housing 180 (FIGS. 17A through 17D) may have a lug slot 192 extending distally from the proximal end 182 thereof, with a lug landing 193 located at a distal end of the lug slot 192. The first syringe sleeve contact surface 262 of the rotary collar 240 supports the syringe sleeve lug 222 before the handle assembly 20 is attached to the syringe housing assembly 160. The lug locking arm 194 extends obliquely into the lug slot 192 to block proximal movement of the syringe sleeve lug 222 and has an angled side contact surface 195 (FIG. 8A). When the handle assembly 20 is attached to the syringe housing assembly 160 in the first syringe sleeve position, a handle pusher lug 136 presses against the angled contact surface 195 and moves the lug locking arm 194 from extending obliquely into the lug slot 192, unlocking the syringe sleeve lug 222 to move proximally to the second syringe sleeve position as the user advances the handle assembly 40 distally and the injection device 10 into the third configuration (FIGS. 10A and 10B, before injection; FIGS. 11A and 11B, after injection). The lug locking arm 194 may again extend obliquely into the lug slot 192 when the handle assembly 20 is detached from the syringe housing assembly 160 after injection to block proximal movement of the syringe sleeve lug 222. The syringe housing 180 may have a viewing window 196 allowing observation of a visual indicator of the progress of the injection.

Figure 2:
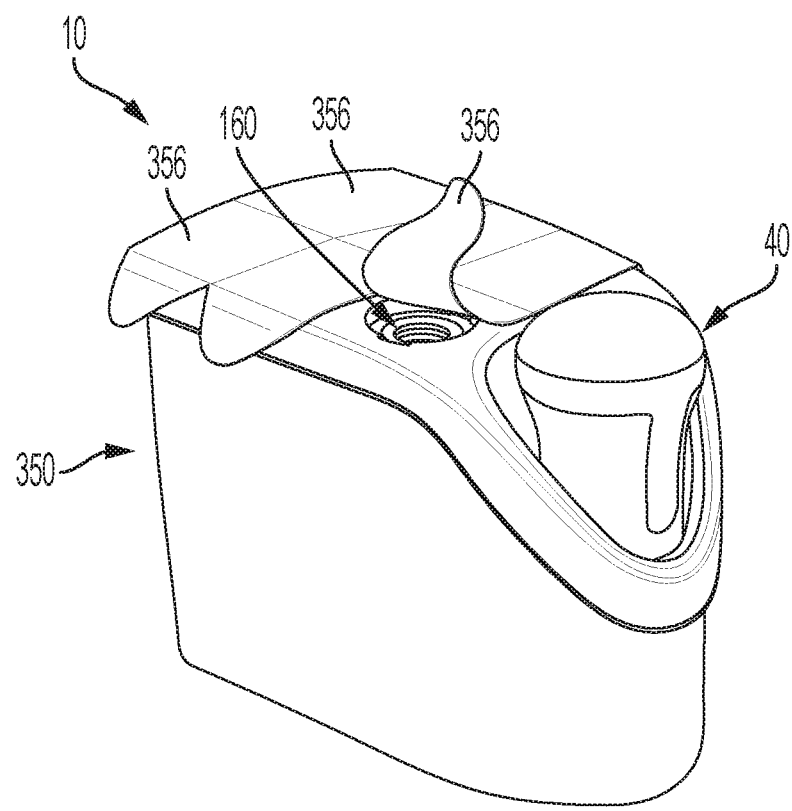
FIG. 2 is a left front perspective view of the injection system of FIG. 1, with a foil cover thereof being removed.
Figure 3:
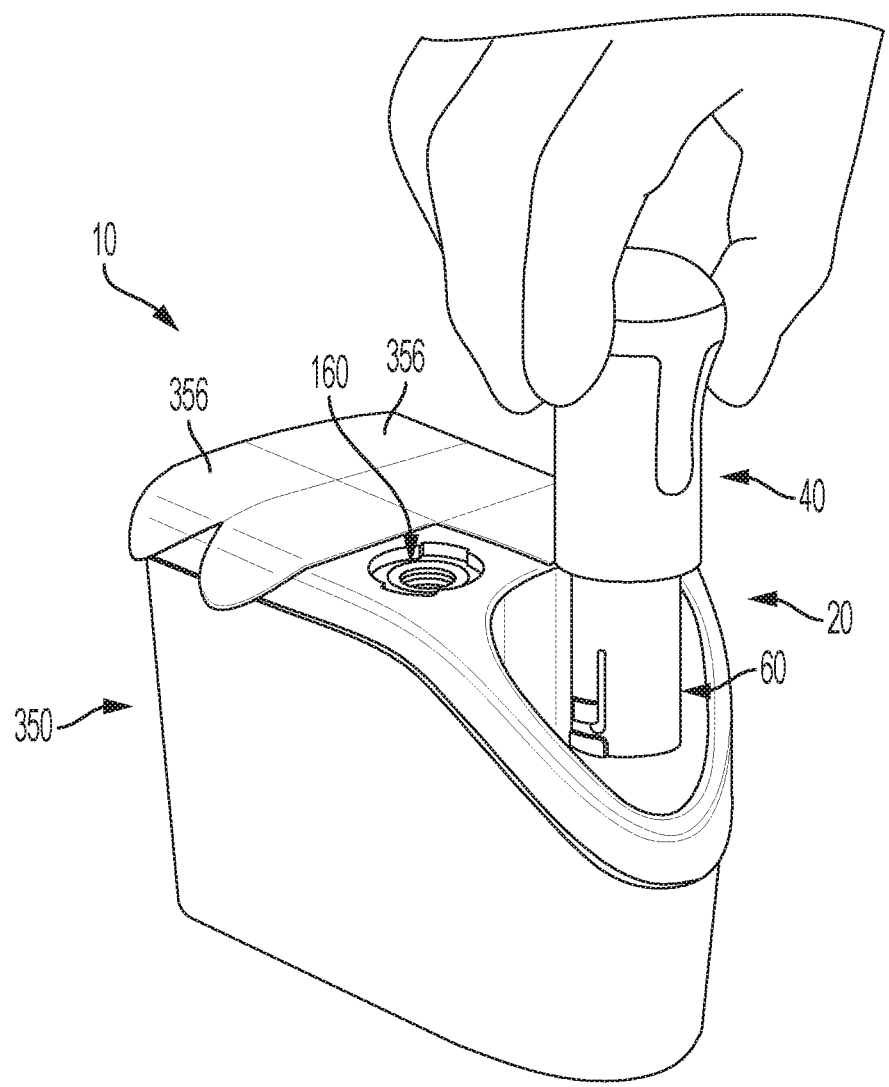
FIG. 3 a left front perspective view of the injection system of FIG. 1, with a handle assembly being removed from a tray by a user.
Figure 4:
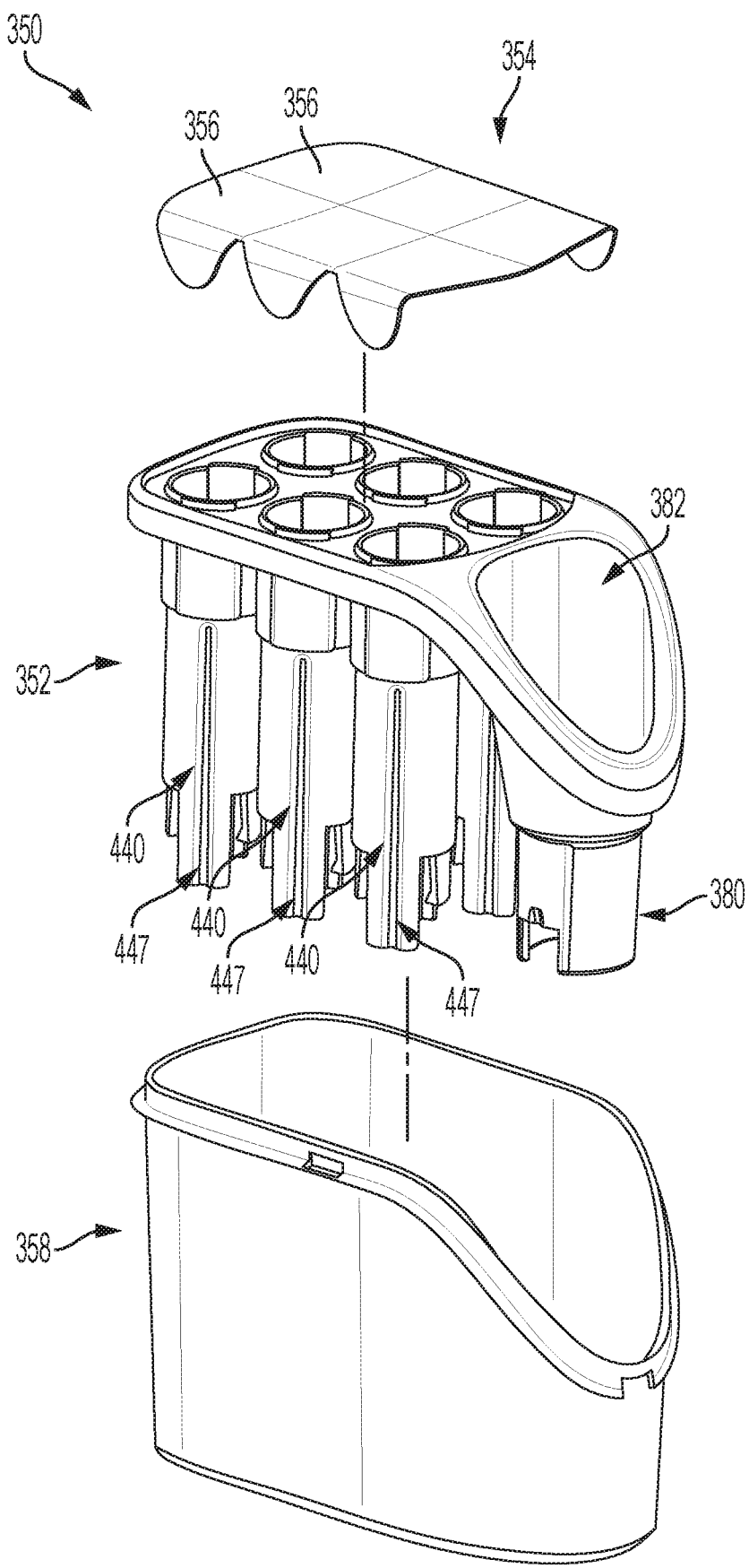
FIG. 4 is an exploded partial perspective view of a tray for use in the system of FIG. 1.
Figure 5:
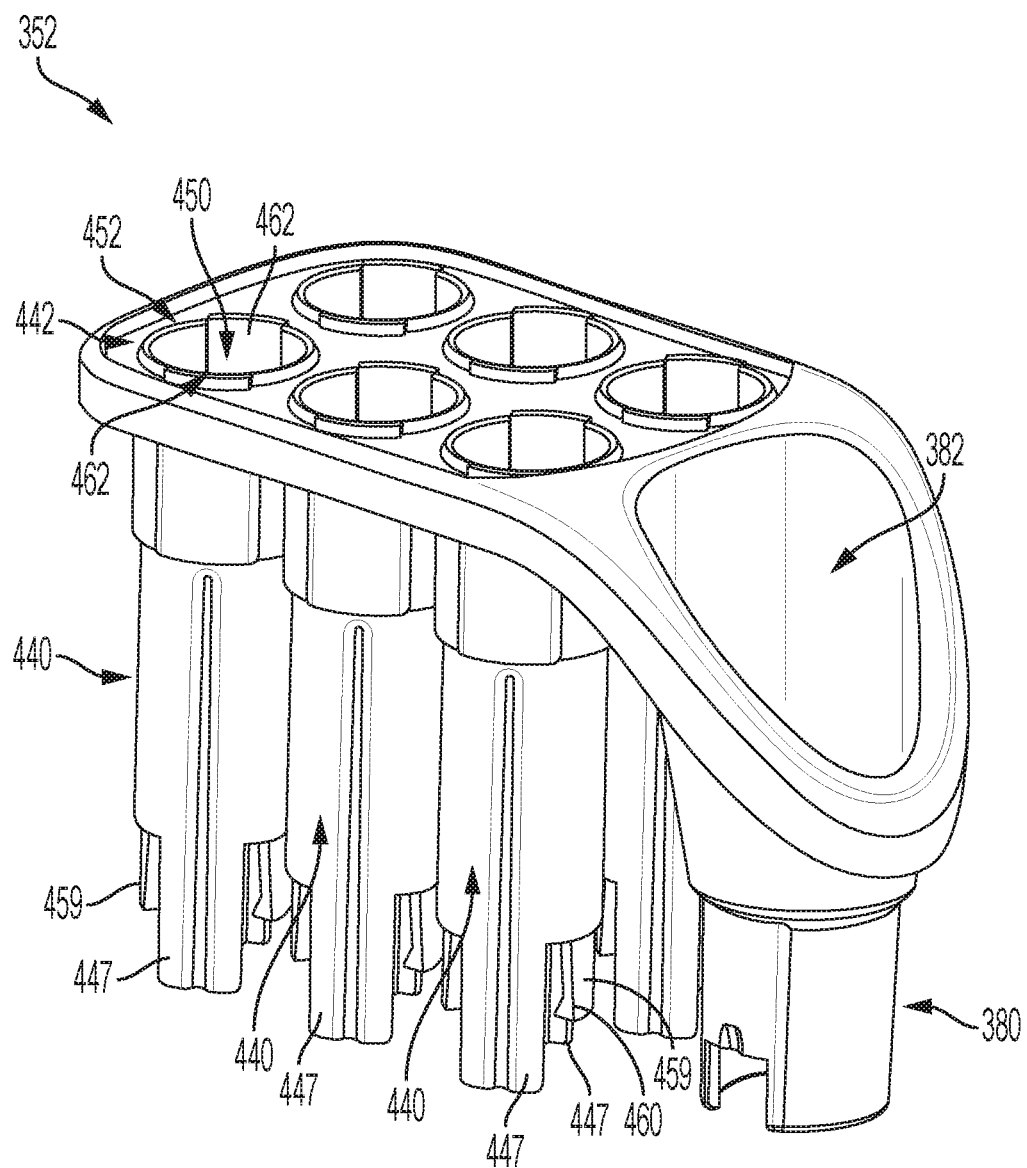
FIG. 5 is a left front perspective view of a nest for use in the system of FIG. 1.
Figure 6:
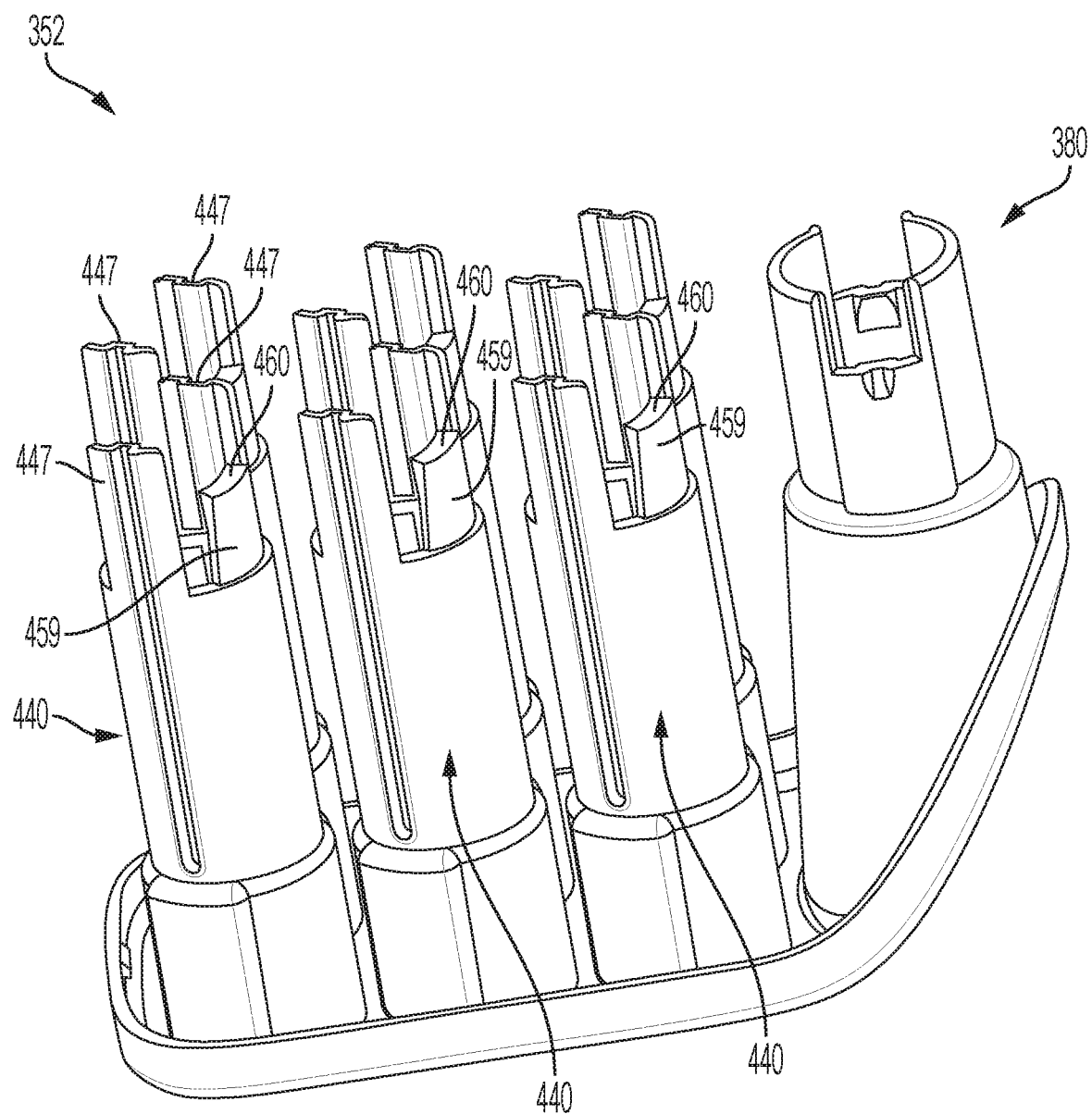
FIG. 6 is an inverted view of the nest of FIG. 5.
Figure 7A:
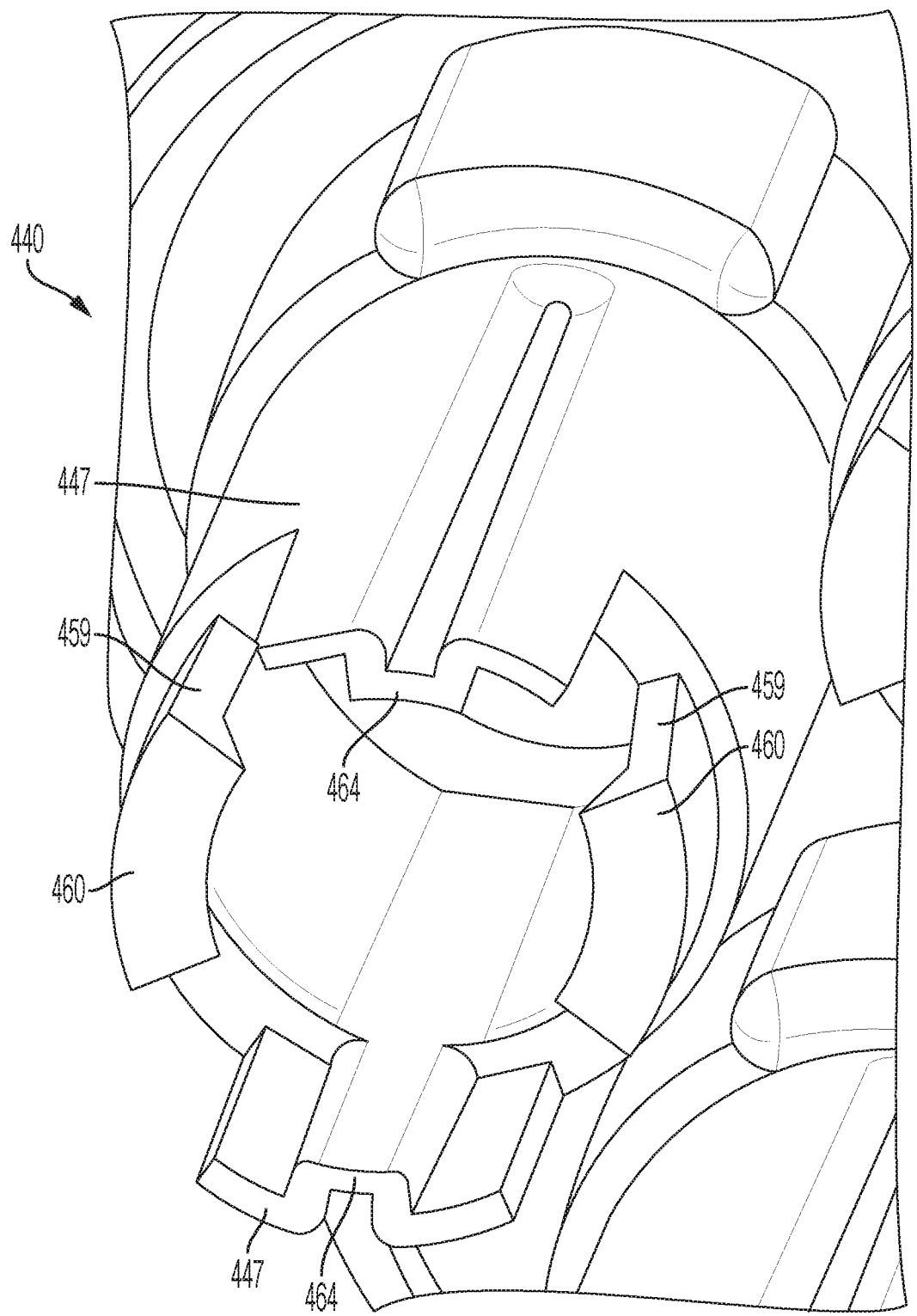
FIG. 7A is a magnified partial view of the nest of FIG. 5.
Figure 7B:
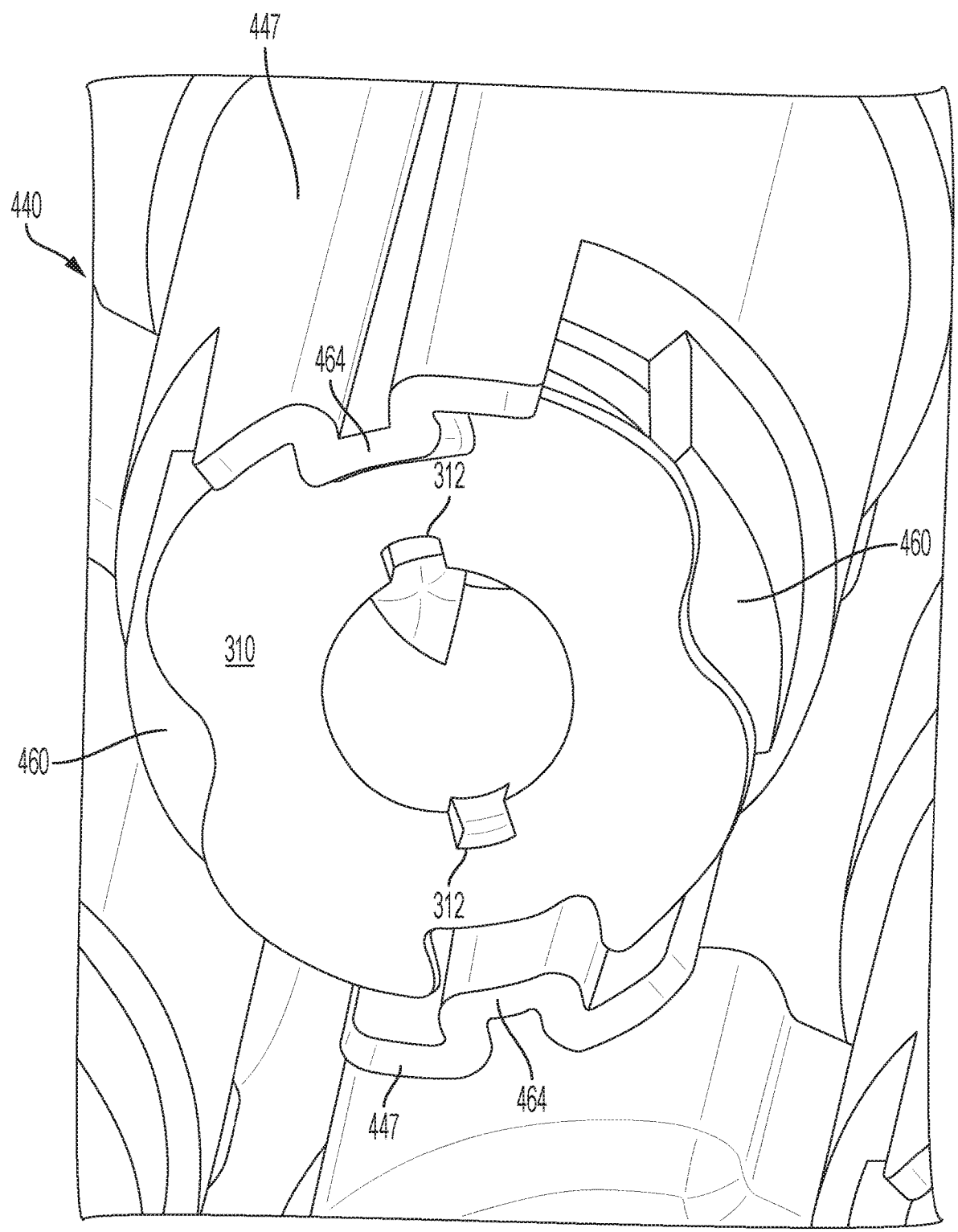
FIG. 7B is a magnified partial view of the nest of FIG. 5 with a needle shield puller secured therein.
Figure 7C:
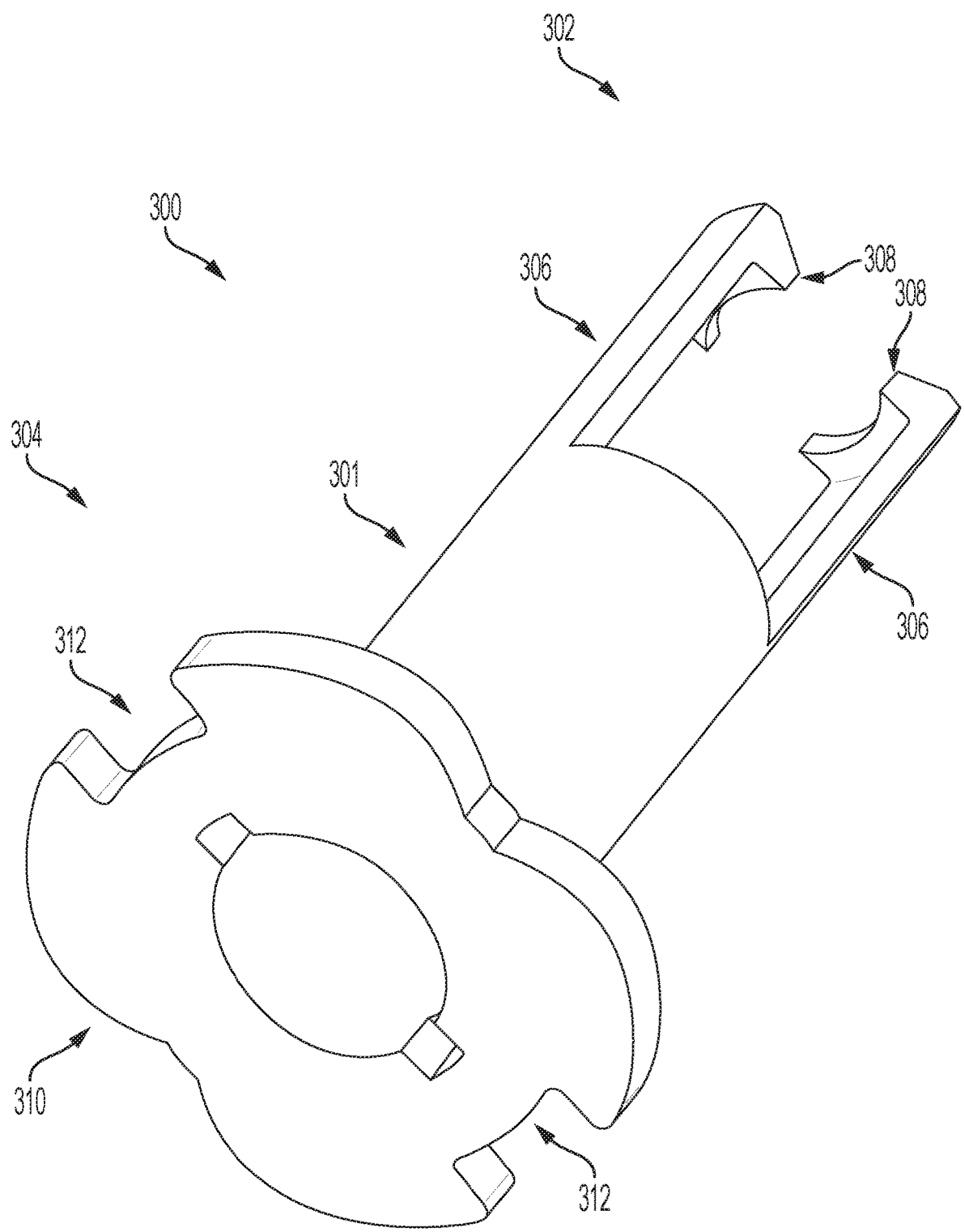
FIG. 7C is a perspective view of the needle shield puller of FIG. 7B.
Figure 7D:
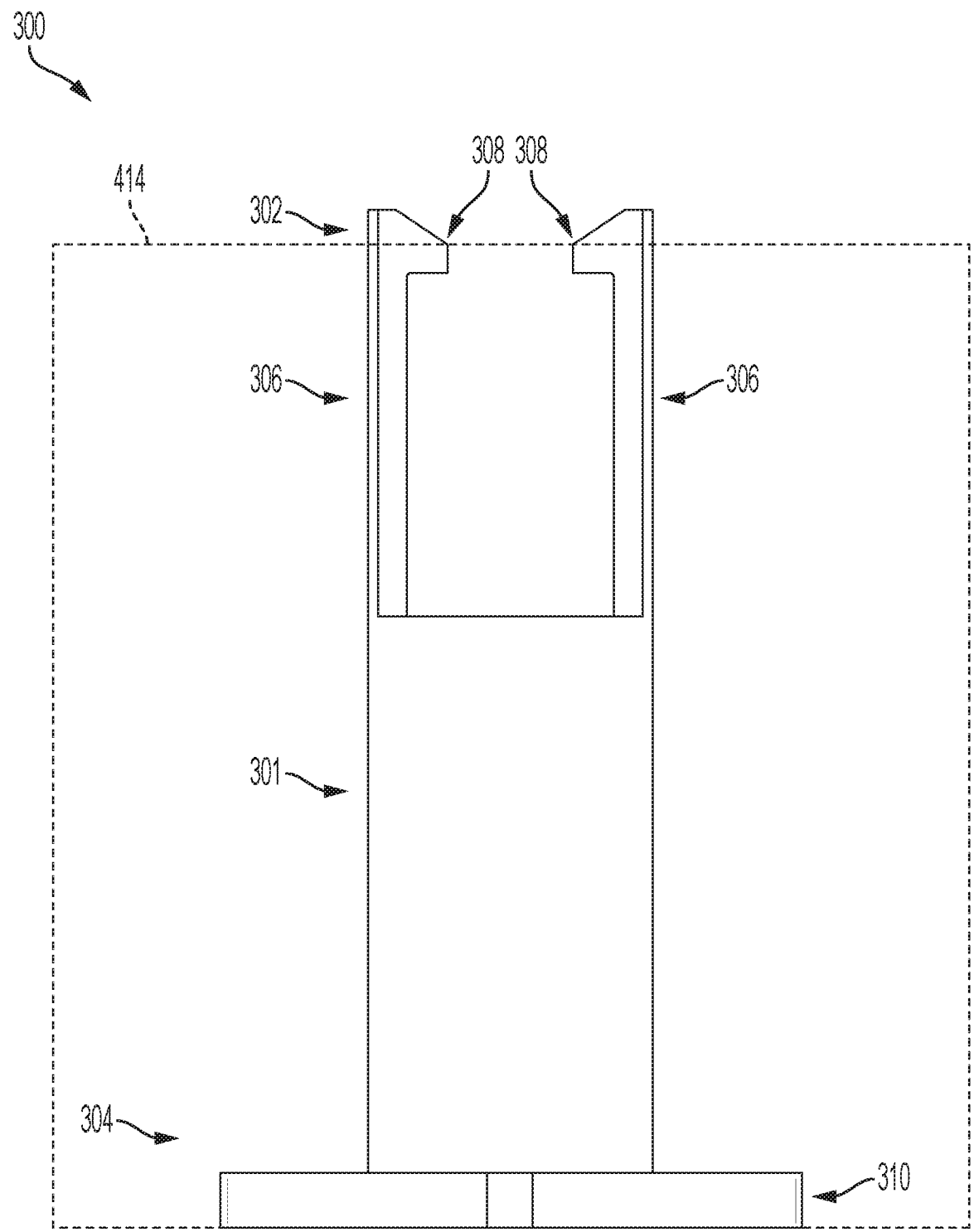
FIG. 7D is an elevational view of the needle shield puller of FIG. 7B.

The injection system 10 has a first configuration wherein the handle assembly 20 is disconnected from the syringe housing assembly 40, as shown in any of FIGS. 1 through 3, and the syringe sleeve 210 is in the first syringe sleeve position, which is the position shown in FIGS. 9A and 9B. The first position is a pre-injection position in which the handle assembly 20 has not yet been connected to a particular syringe housing assembly 160, although naturally the handle assembly 20, which is preferably configured to be reusable, may have been used previously with another syringe housing assembly 160.

The injection system 10 has a second configuration wherein the handle assembly 20 is connected to the syringe housing assembly 160 and the syringe sleeve 210 is in the first syringe sleeve position, as shown in FIGS. 9A and 9B. The injection system in the second configuration is safe for the user to handle because the syringe sleeve 210 extends distally beyond the needle tip 278 sufficiently that the needle tip 278 is unlikely to accidentally penetrate a skin surface. As shown in FIGS. 9A and 9B, the injection system 10 in the second configuration is ready to be placed against a skin surface 12 for an injection.

Figure 10A:
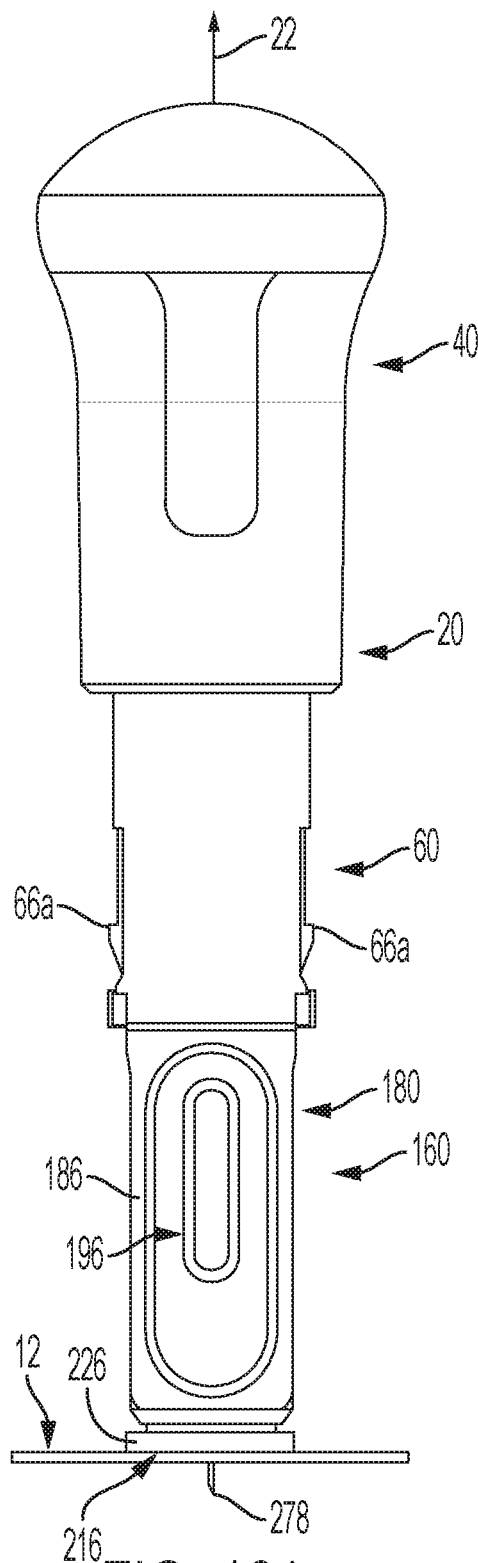
FIGS. 10A and 10B are front elevational and sectional views of the handle assembly and syringe housing assembly from the system of FIG. 1 in contact with the skin surface, with the syringe sleeve in a second position and a needle protruding distally through the skin surface, prior to beginning an injection.
Figure 10B:
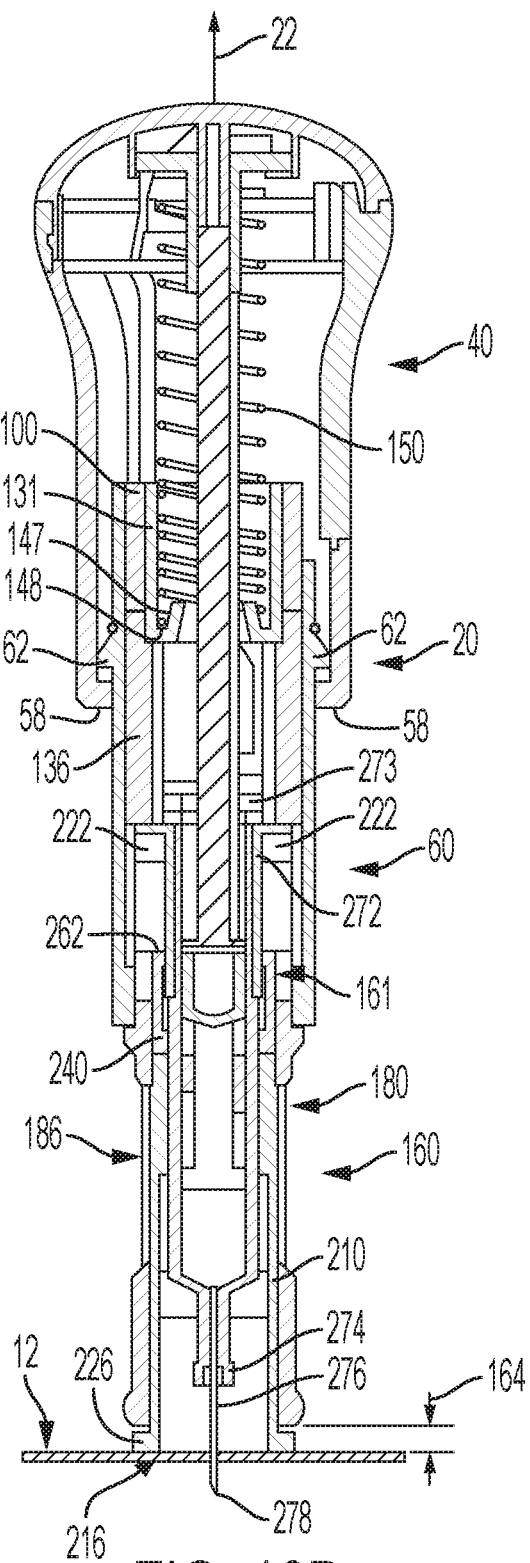
Figure 11A:
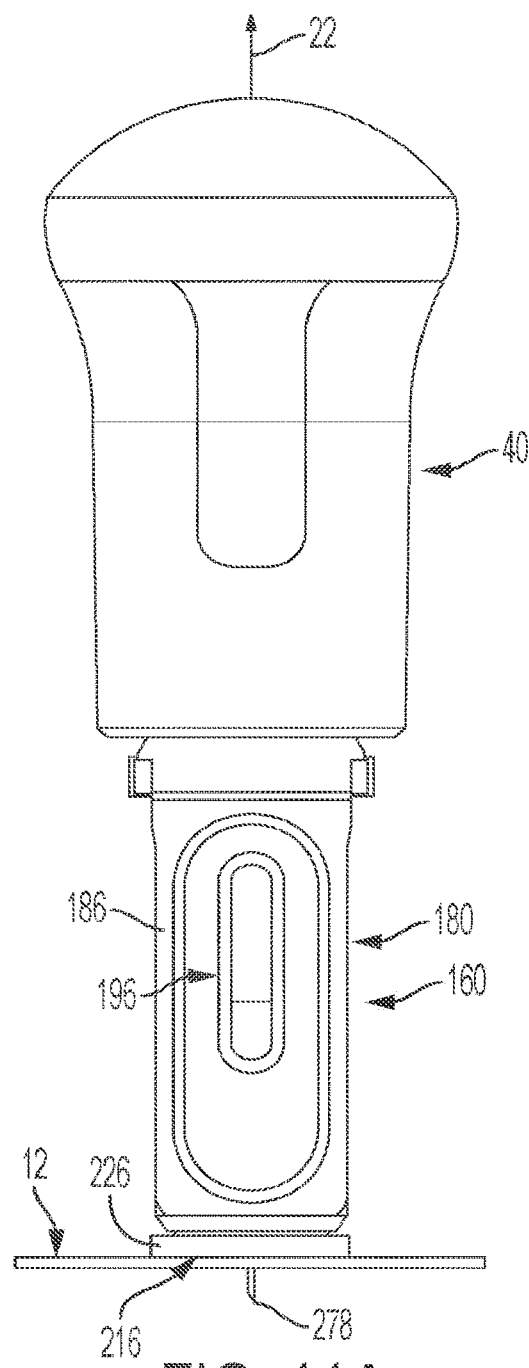
FIGS. 11A and 11B are front elevational and sectional views of the handle assembly and syringe housing assembly from the system of FIG. 1 in contact with the skin surface, with the syringe sleeve in the second position and the needle protruding distally through the skin surface, upon completion of the injection.
Figure 11B:
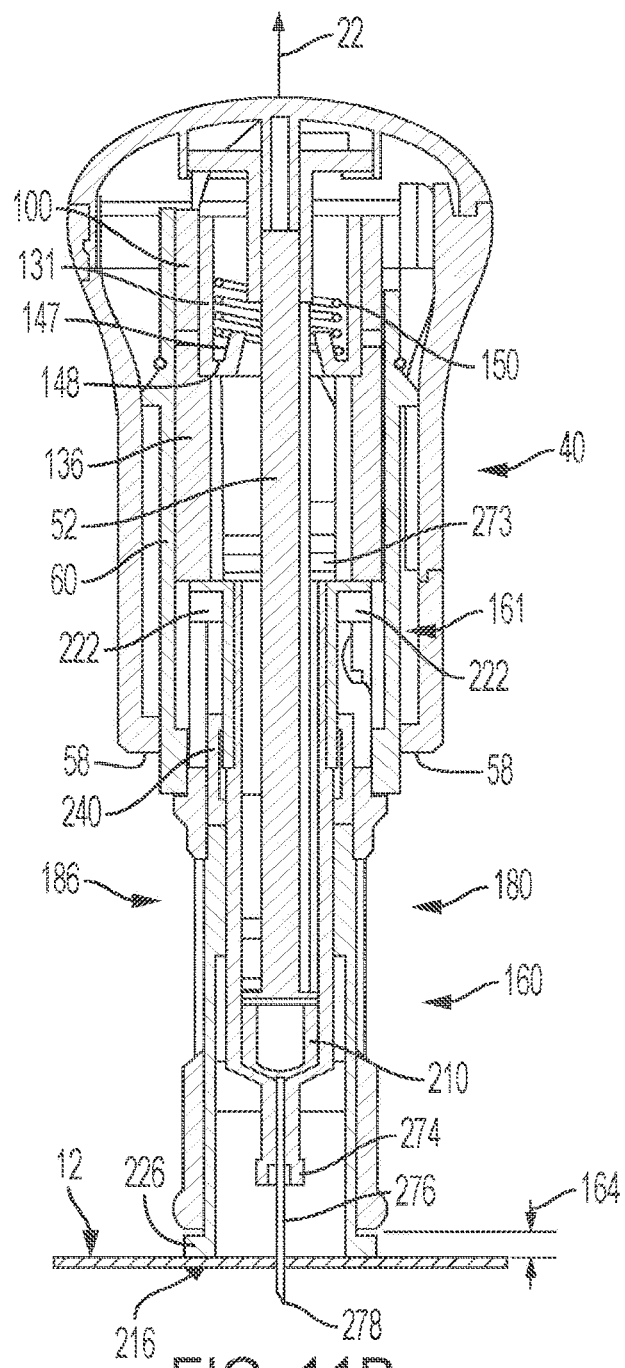
Figure 12A:
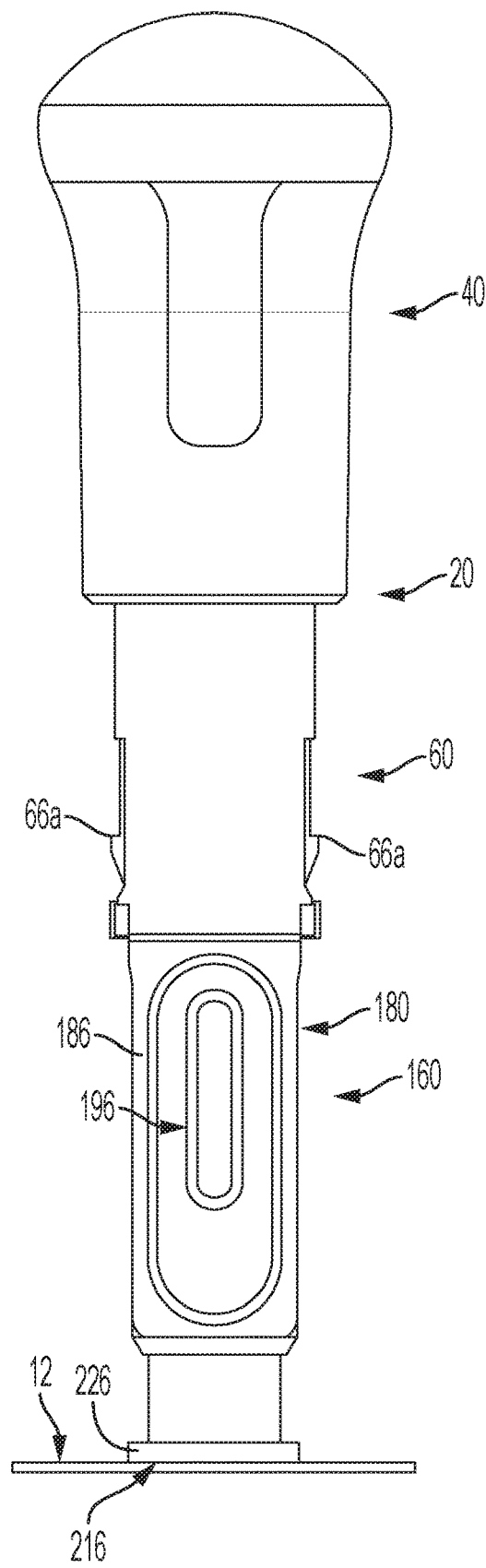
FIGS. 12A and 12B are front elevational and sectional views of the handle assembly and syringe housing assembly from the system of FIG. 1 in contact with the skin surface, with the syringe sleeve in a third position and the needle covered by the syringe sleeve, upon removal from the skin surface.
Figure 12B:
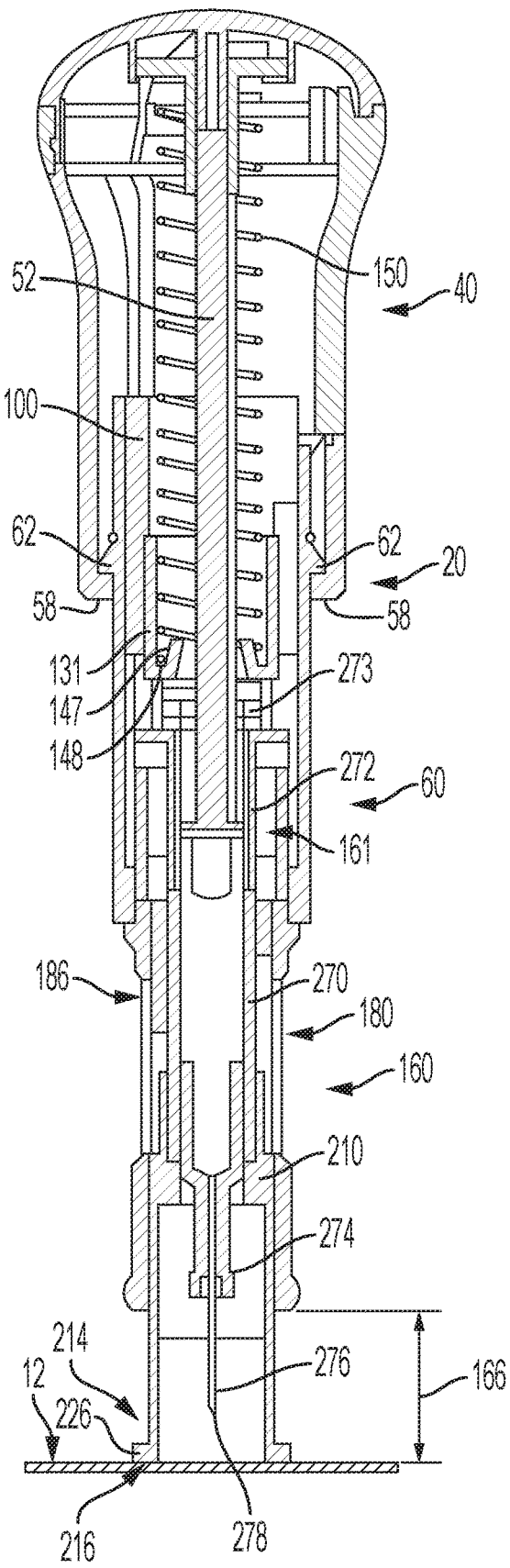
Figure 13A:
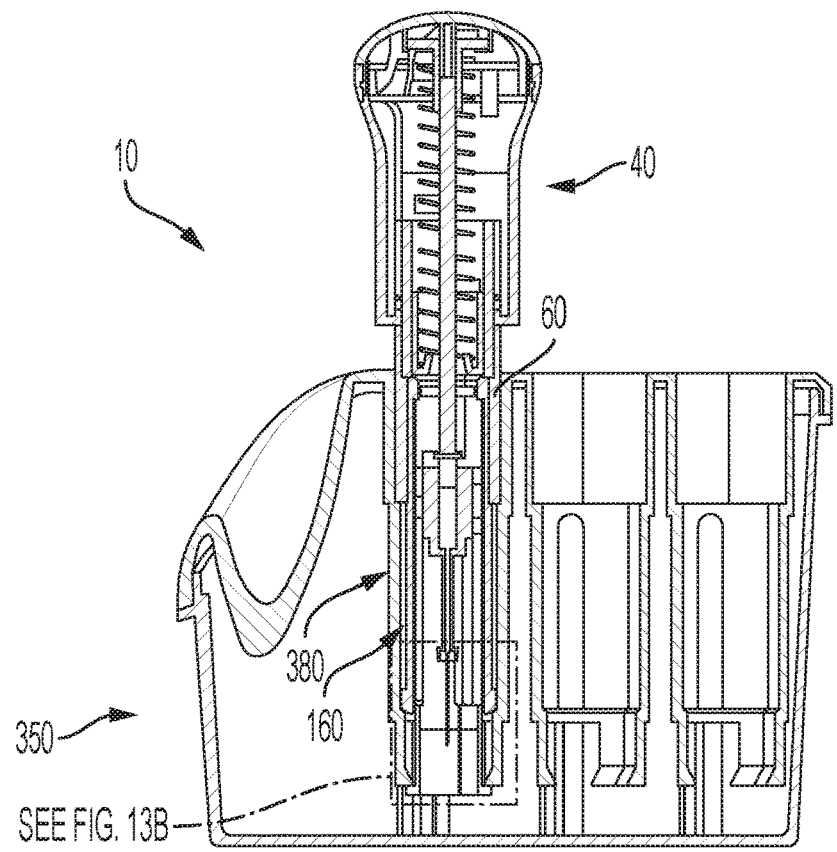
FIG. 13A is a right side sectional view of the system of FIG. 1, with the handle assembly engaged with the syringe housing in the tray, and with the syringe sleeve advanced to the third position.
Figure 13B:
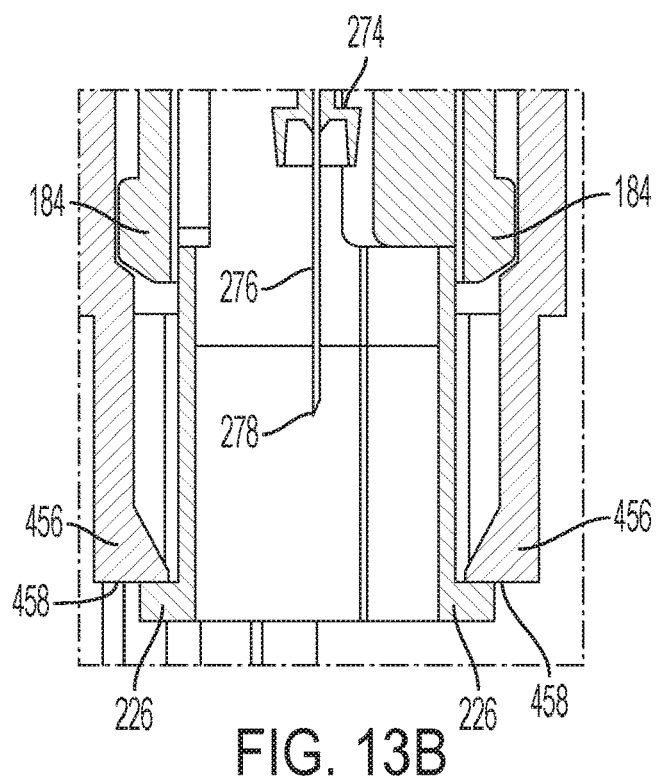
FIG. 13B is a magnified portion of the sectional view of FIG. 13B.

The injection system 10 has a third configuration wherein the handle assembly is connected to the syringe housing assembly and the syringe sleeve is in the second syringe sleeve position, as shown in FIGS. 10A and 10B (a subconfiguration of the third configuration, before injection) and FIGS. 11A and 11B (another subconfiguration of the third configuration, after injection). The injection system 10 has a fourth configuration wherein the handle assembly 20 is connected to the syringe housing assembly 160 and the syringe sleeve 210 is in the third syringe sleeve position, as shown in FIGS. 12A and 12B (a subconfiguration of the fourth configuration, after injection, with the injection system 10 about to be removed from the skin surface). The injection system 10 has a fifth configuration wherein the handle assembly 20 is disconnected from the syringe housing assembly 160 and the syringe sleeve 210 is in the third syringe sleeve position, and as shown in FIGS. 13A and 13B, after injection, with the syringe housing assembly 160 preferably engaging a locking projection 456 of the storage tube 440, as discussed below, preferably in a tray 350.

Figure 19A:
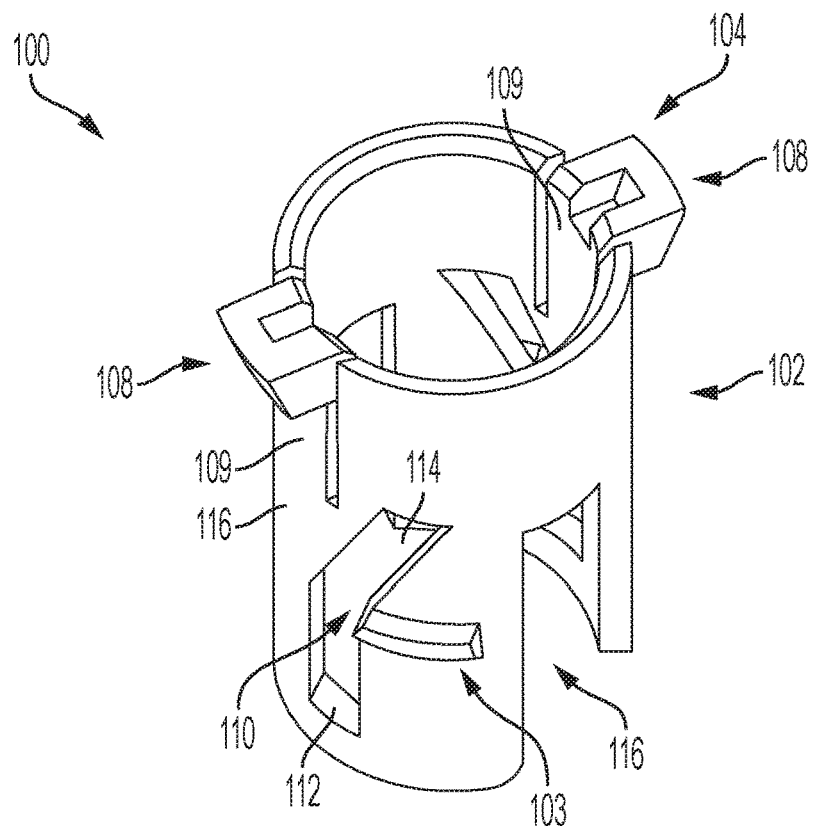
FIG. 19A is a perspective view of a handle barrel for use in the system of FIG. 1.
Figures 19B, 19C:
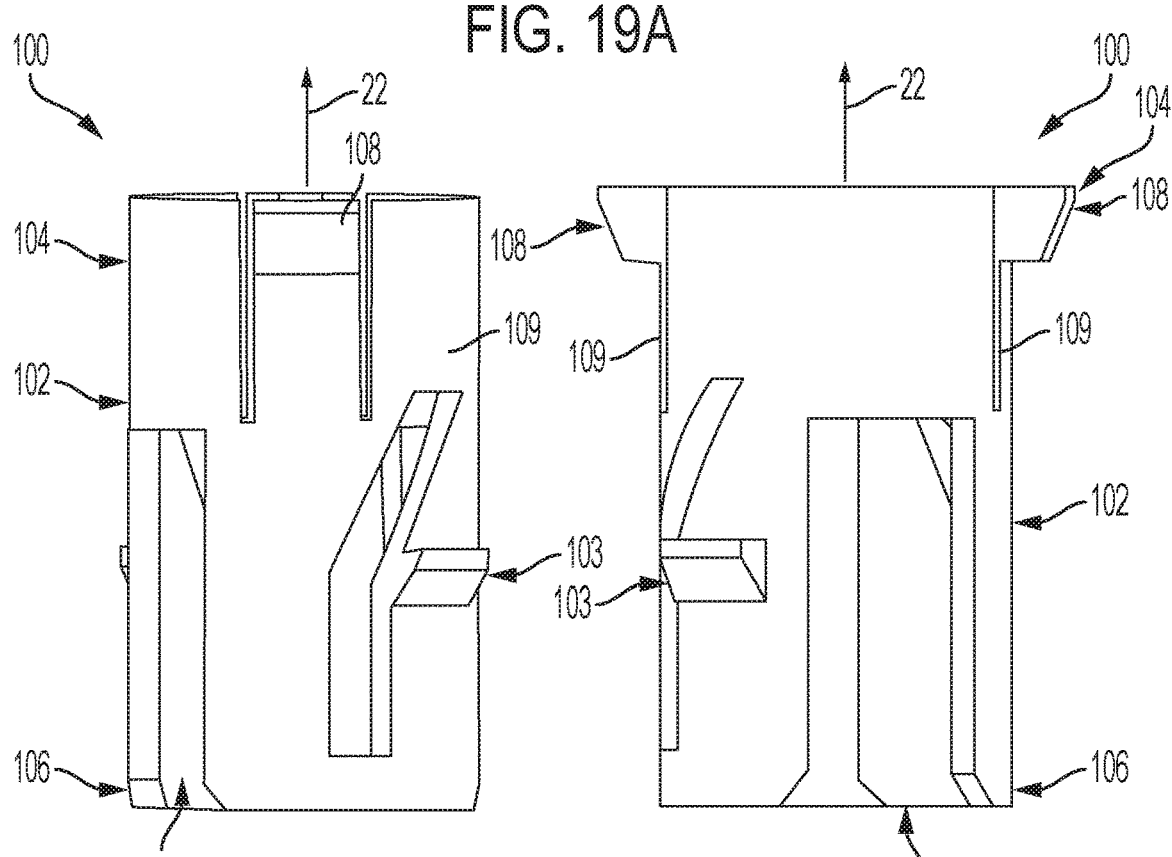
FIGS. 19B and 19C are left side and front elevational views of the handle barrel of FIG. 19A.

Referring to FIGS. 19A through 19C, the handle barrel 100 may be rotatably mounted and axially fixed with respect to the handle collar 60. An axial support tab 103, or another suitable support structure, fixes the handle barrel 100 axially while permitting axial rotation thereof. In the embodiment shown, the handle barrel 100 has a generally cylindrical sidewall 102 extending between a proximal end 104 and a distal end 106 of the handle barrel 100. A handle body landing 108 on an axially extending arm 109 preferably extends radially outwardly from the sidewall 102. The handle barrel 100 is rotatable with respect to the handle body 40 between a first and a second handle barrel position. In the first handle barrel position, which the handle barrel 100 assumes when the injection system 10 is in the first, second, fourth, and fifth configurations, the handle body landing 108 is circumferentially aligned with and engages the radially extending corresponding handle body projection 54 of the handle body 40 to restrain a distal relative movement of the handle body 40 with respect to the handle collar 60. In the second handle barrel position, which occurs when the injection system is in the third configuration, the handle body landing 108 is out of circumferential alignment with the corresponding handle body projection 54 such that the handle body 40 is free to move distally with respect to the handle collar 60. The handle barrel 100 hay have a handle barrel track 110 arranged on the sidewall 102 of the handle barrel 100. The handle barrel track 110 is oriented at least partially non parallel to the longitudinal axis 22 between a first end 112 and a second end 114 of the handle barrel track 110. An axial slot 116 extends proximally from the distal end 106 and accommodates the syringe sleeve lug 222.

Referring to FIGS. 9B, 20A, and 20B, the injection system 10 may also include a handle pusher 130 having a proximal end 132 and a distal end 134, a cylindrical body 131, and a pair of handle pusher lugs 136 at the distal end 134. In the illustrated embodiment, the lugs 136 are elongated and distally attached to the body 131 and have tracks 144 to maintain the handle pusher 130 in alignment with the handle collar 60. The body 131 has a central bore 133 in an internal frusto-conical body with a sloped surface 147 and a groove 148 (FIGS. 9B, 10B, 11B, 12B), which in the illustrated embodiment serves as a seat for the spring 150. The bore 133 allows for passage of the plunger 52. The handle pusher 130 is preferably telescopically received within the handle collar 60 and rotatably fixed with respect to the handle collar 60. The handle pusher lug 136 has a distal contact surface 138. The handle pusher 130 has a radially extending handle pusher projection 140 which may be mounted on an axially oriented leg 142. The handle pusher projection 140 extends into the handle barrel track 110 and is movable between the first end 112 and the second end 114 of the handle barrel track 110 such that, upon a proximal relative movement of the handle pusher 130 with respect to the handle collar 60, the handle barrel 100 rotates with respect to the handle collar 60 from the first handle barrel position to the second handle barrel position. Further, upon a distal relative movement of the handle pusher 130 with respect to the handle collar 60, the handle barrel 100 rotates with respect to the handle collar 60 from the second barrel handle position back to the first barrel handle position.

Referring to FIGS. 9B and 16A through 16C, the rotary collar 240 may be rotatably mounted and axially fixed within the syringe housing interior 188 by a support tab 243 extending radially from an arm 241. The rotary collar 240 may have a proximal end 242, a distal end 244, a distal surface 260, a generally cylindrical sidewall 246, and a cam surface 248 formed in the sidewall 246. At least a portion of the cam surface 248 extends from a first cam end 250 proximate the distal end 244 of the rotary collar 240 to a second cam end 252 that is spaced apart proximally and circumferentially from the first cam end 250. The rotary collar 240 further includes a flexible locking arm 254 extending axially toward a free end 256 with a distally facing locking surface 258 that is distally located from a distal surface 260 of the rotary collar 240. The free end 256 may also have a radially, inwardly facing angled ramp 261. The locking pin 220 of the syringe sleeve 210 may be in contact with the cam surface 248 at the first cam end 250 when the syringe sleeve 210 is in the first syringe sleeve position such that, upon proximal movement of the syringe sleeve 210 with respect to the syringe housing 180 from the first syringe sleeve position to the second syringe sleeve position, the locking pin 220 interacts with the cam surface 248 to rotate the rotary collar 240 with respect to the syringe housing 180 from a first rotary collar position to a second rotary collar position. In the second rotary collar position, the locking pin 220 may cease contact with the cam surface 248 at the second cam end 252 and may be circumferentially aligned with the locking arm 254 with the syringe sleeve 210 is in the second syringe sleeve position. Upon subsequent distal movement of the syringe sleeve 210 with respect to the syringe housing 180 to the third syringe sleeve position, the locking pin 220 moves distally with respect to the rotary collar 240 along the locking arm 254 until the locking pin 220 passes over the angled ramp 261 and snaps onto the locking surface 258 of the locking arm 254, at which time the locking surface 258 prevents the locking pin 220 from moving proximally with respect to the rotary collar 240, locking the syringe sleeve in the third syringe sleeve position.

In some embodiments of the invention, the rotary collar 240 is in the first rotary collar position when the syringe sleeve 210 is in the first syringe sleeve position and is in the second rotary collar position when the syringe sleeve 210 is in the second and third syringe sleeve positions. The rotary collar 240 may have a first proximally facing syringe sleeve contact surface 262, and a second proximally facing syringe sleeve contact surface 264. The first syringe sleeve contact surface 262 may be in contact with a distally facing surface 224 of the syringe sleeve lug 222 when the rotary collar 240 is in the first rotary collar position and the syringe sleeve 210 is in the first syringe sleeve position to prevent distal movement of the syringe sleeve 210 with respect to the syringe housing 180. The second syringe sleeve contact surface 264 may be being in contact with the distally facing surface 224 of the syringe sleeve lug 222 when the rotary collar is in the second position and the syringe sleeve 210 is in the third syringe sleeve position to prevent distal movement of the syringe sleeve 210 with respect to the syringe housing 180.

Referring to FIGS. 5, 6, 8A, 8D, and 8E, the storage tube 440 may include a storage tube body 442 having a proximal end 444, a distal end 446, a side wall 448, and a cavity 450 accessible through an opening 452 (FIG. 5) at the proximal end 444 of the storage tube body 442 for accepting the syringe housing assembly 160. A syringe housing assembly landing 454 is preferably located within the cavity and supports the syringe housing assembly 160 in the cavity 450. A syringe housing assembly lock in the form of a radially extending locking projection 456 is located within the cavity 450 at an axial position within the storage tube body 442 such that, when the syringe housing assembly 160 is supported by the syringe housing assembly landing 454 and the syringe sleeve 210 is in the first syringe sleeve position, the locking projection 456 does not engage the locking flange 226 of the syringe sleeve 210. When the syringe housing assembly 160 is supported by the syringe housing assembly landing 454 and the syringe sleeve 210 is in the third syringe sleeve position, the locking projection 456 preferably engages the locking flange 226 of the syringe sleeve 210 and locks the syringe housing assembly 160 against removal from the storage tube 440. A distance between the proximal end 444 of the storage tube body 442 and the locking projection 456 is sufficient that the proximal end 161 of the syringe housing assembly 160 is countersunk distally from the proximal end 444 of the storage tube 442.

Figure 8C:
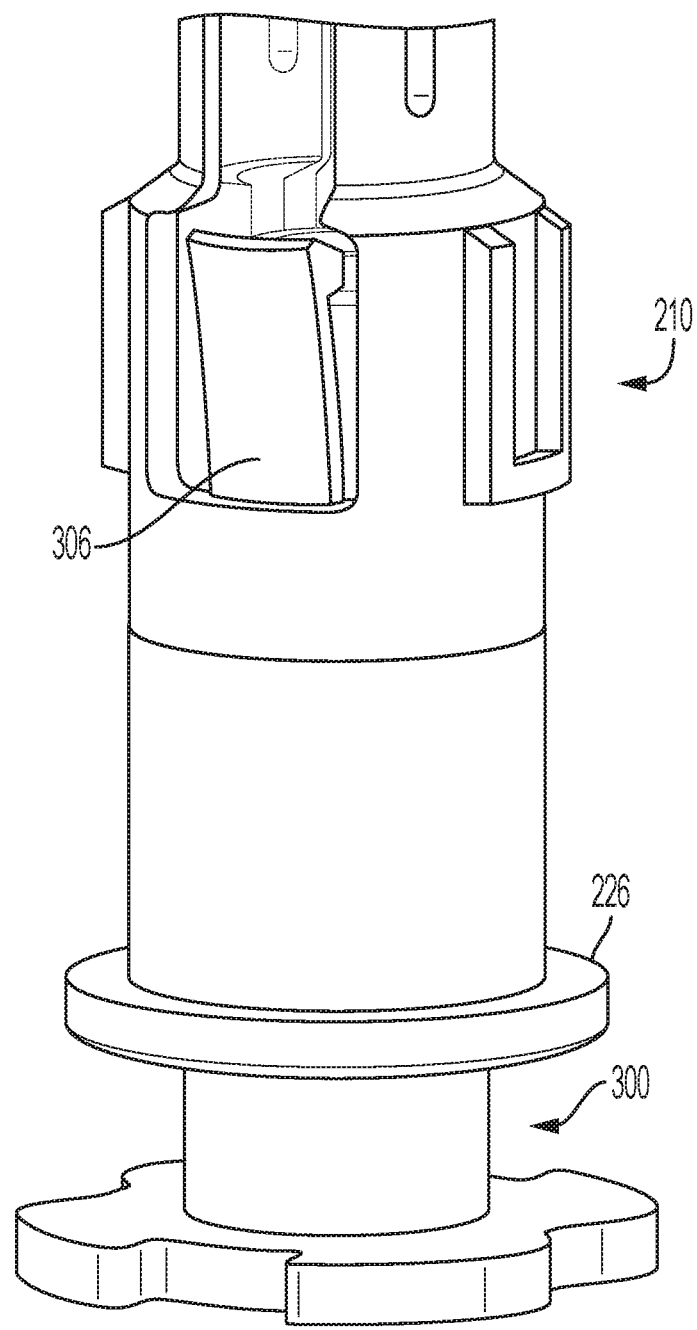
FIG. 8C is a partial perspective view of the needle shield puller and syringe sleeve of the system of FIG. 1.
Figure 8D:
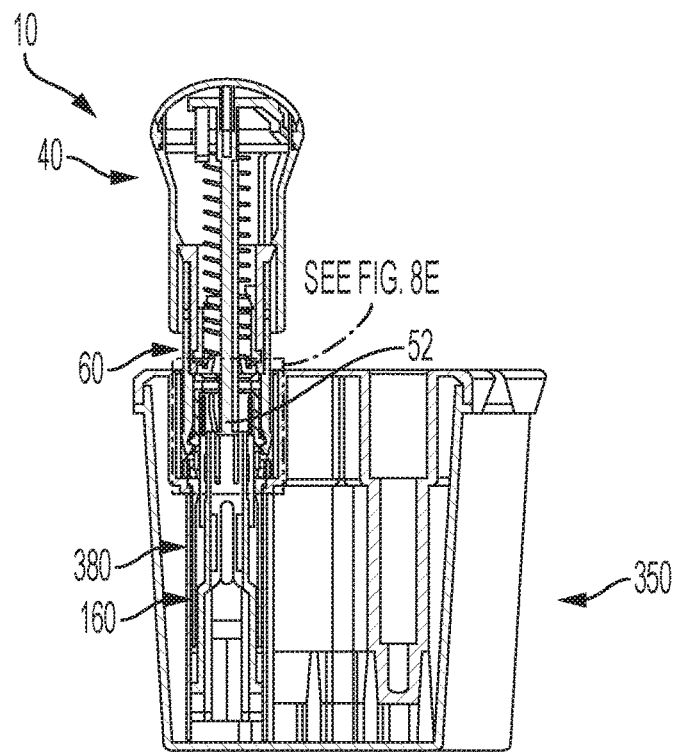
FIG. 8D is a left side sectional view of the system of FIG. 1, with the handle assembly engaged with a syringe housing in the tray and the syringe sleeve in a first position.
Figure 8E:
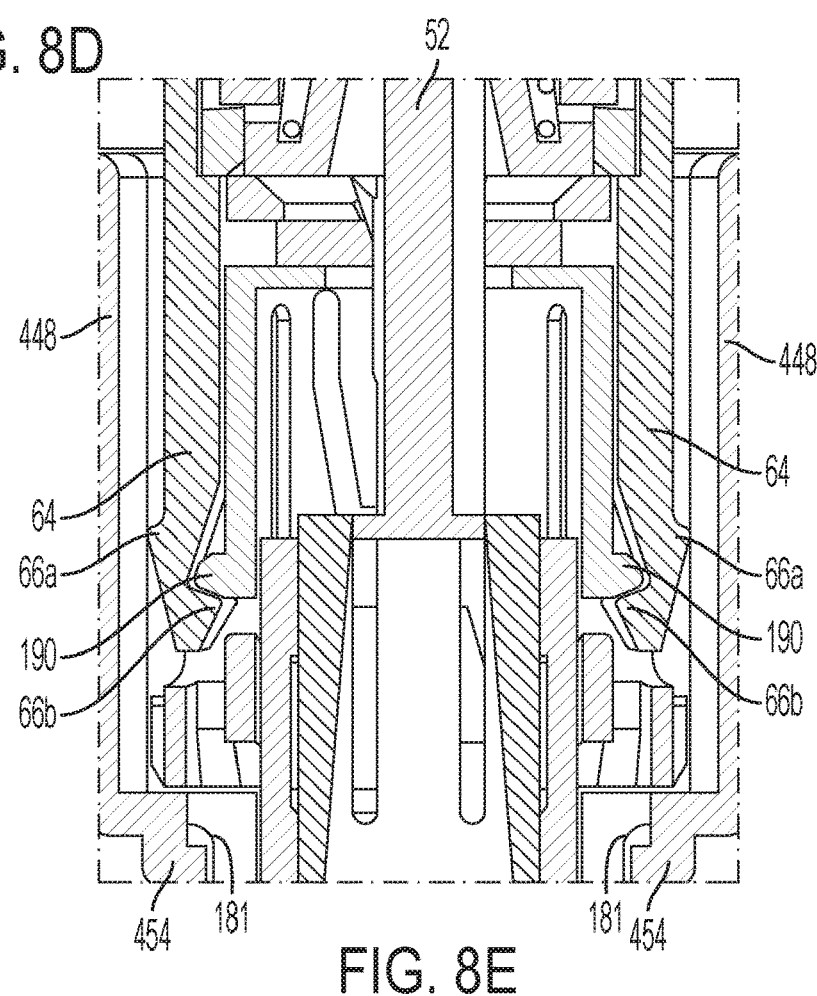
FIG. 8E is a magnified portion of the sectional view of FIG. 8D.
Figure 8F:
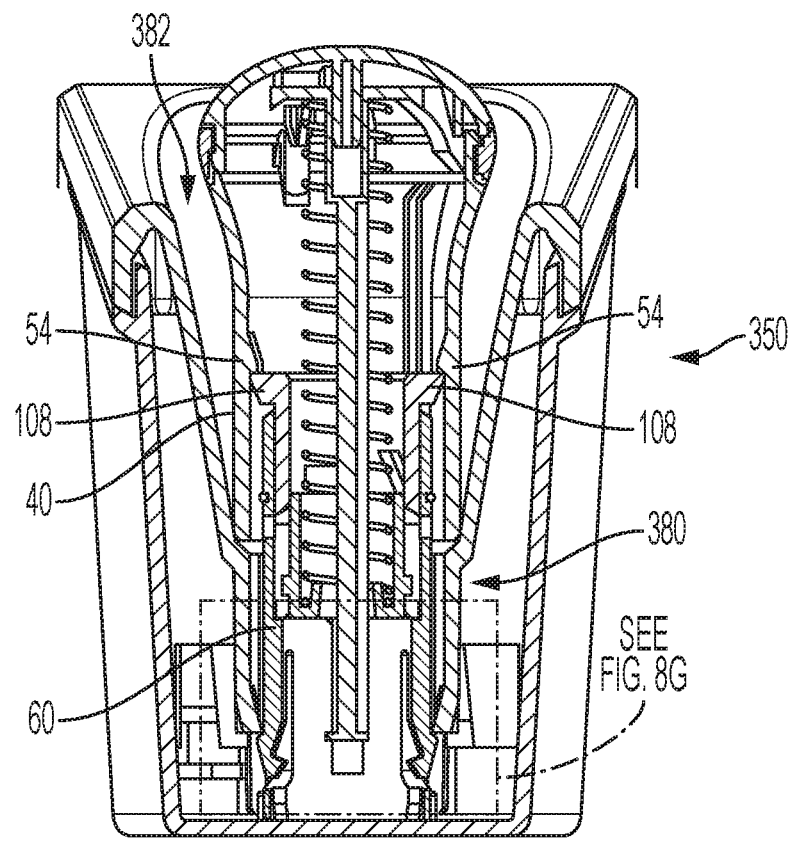
FIG. 8F is a front side sectional view of the system of FIG. 1, with the handle placed in a handle storage tube.
Figure 8G:
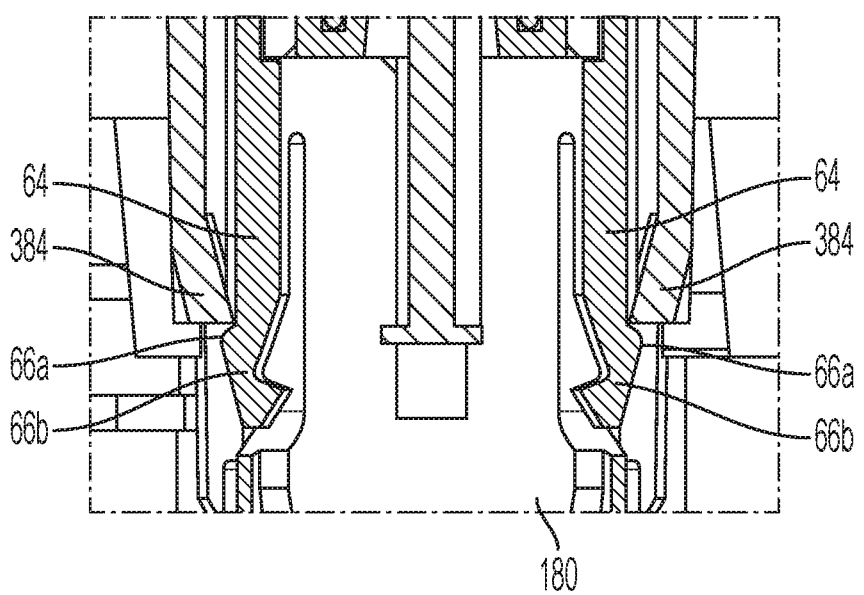
FIG. 8G is a magnified portion of the sectional view of FIG. 8F.

Referring to FIGS. 7A through 8C, a needle shield puller 300 may be disposed within the cavity 450 of the storage tube 440 and configured to attach to the needle shield 280, such that upon a proximal relative movement of the syringe housing assembly 160 with respect to the storage tube 440, the needle shield 280 is removed from the distal end 274 of the syringe 270. The needle shield puller 300 has cylindrical body 301 with a proximal end 301 and a distal end 304. The needle shield puller 300 has a proximally extending arm 306 with a tooth 308 disposed at a free end thereof. The needle shield puller 300 has a distally located base plate 310 with a locking notch 312 therein. In the illustrated embodiment, the base plate 310 is eccentrically shaped. In the embodiment of FIGS. 8A through 8C, the needle shield 280 has a circumferential projection in the form of a flange 282 engagable by a tooth 308 on a flexible, proximally extending arm 306 of the needle shield puller 300. The needle shield puller 300 slidably fits within the syringe sleeve 210, passing through an axial opening 215 in the distal end of the needle shield puller 300 into the interior of the syringe sleeve 210 to engage the needle shield 280. The syringe sleeve 210 has an inner surface 228 and a pair of opposing windows 230 each selectively alignable with a respective flexible arms 306 of the needle shield puller 300 so that in a first needle shield position, each flexible arm 306 is aligned with the respective window 230 and flexes radially outwardly to allow the tooth 308 of the flexible arm 306 to move past the flange 282 of the needle shield 280, and in a second needle shield position, each arm 306 is at least partially unaligned with the respective window 230 such that the inner surface 228 of the syringe sleeve 210 prevents the flexible arm 306 from flexing sufficiently radially outwardly to permit the flange 282 of the needle shield 280 to pass, thereby locking the needle shield puller 300 to the needle shield 280. The force required to remove the needle shield 280 from the syringe 270 may be adjusted to ensure that the needle shield 280 becomes detached from the syringe 270 upon an axial movement of the syringe housing assembly 260 when the needle shield 280 is in the second needle shield position.

Figure 14A:
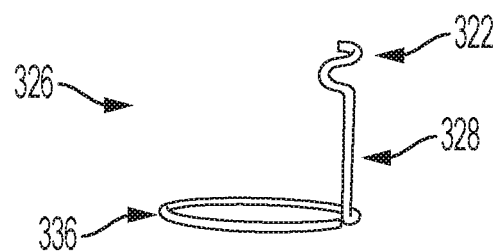
FIG. 14A is a perspective view of a biasing member and striker for use in the system of FIG. 1.
Figure 14B:
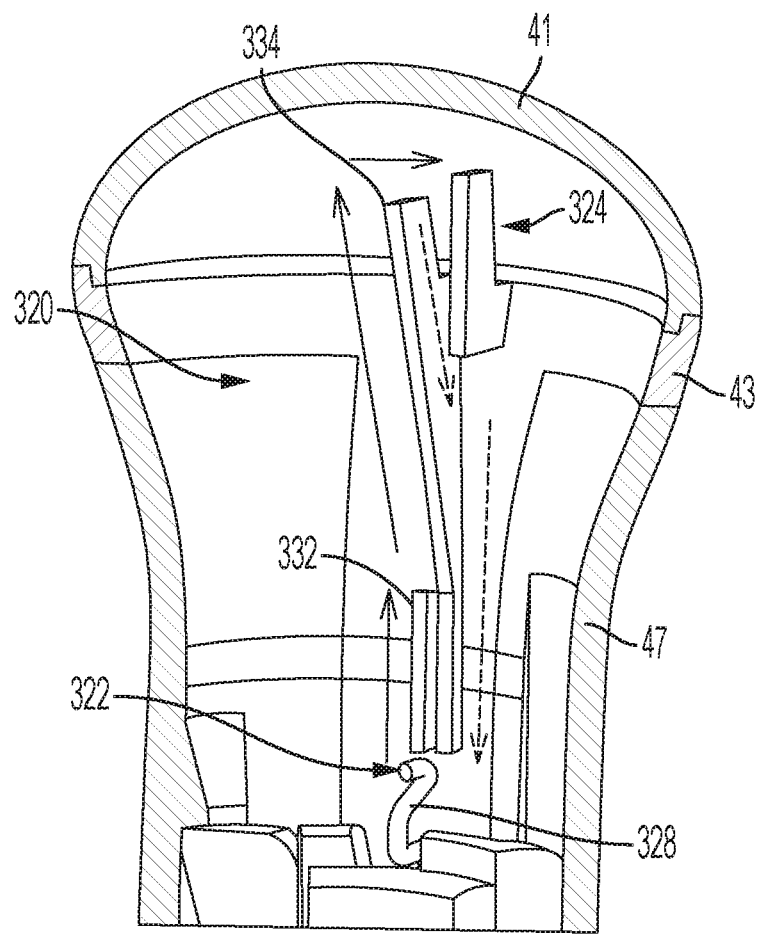
FIG. 14B is a cutaway view of the handle assembly of FIG. 1 showing the striker of FIG. 14A.

The injection system 10 may include an audio alert means configured to provide an audio alert when the handle body 40 reaches an end of injection position such that the handle body 40 cannot move any further distally with respect to the handle collar 60. Referring to FIGS. 14A and 14B, an example of an audio alert means 320 includes a striker 322, a strike plate 324, and an alert biasing member 326 with a resilient arm 328 connected to a support ring 330 and operatively connected to the striker 322. A striker pusher includes a track 332 for directing the striker 322 to an axially angled rail 334 for biasing the striker 322 with respect to the strike plate 324 and releasing the striker 322 to strike the strike plate 324 upon the handle body 40 reaching the end of injection position. The track 332 engages at least one of the alert biasing member 326 and the striker 322, and here engages the resilient arm 328 during movement of the handle body 40 with respect to the handle collar 60, releasing the striker 322 upon the handle body 40 reaching the end of injection position. The biasing member 326 is preferably attached to the handle collar 60 via the support ring 330, and the striker 322 is attached to an end portion 323 of the resilient arm 328 of the biasing member 326. The audio alert means 320 may work in coordination with tactile feedback received from the plunger 52 reaching a distal end of travel within the syringe 270.

Referring to FIGS. 1-7, 18D, and 18E, the injection system may include a tray 350 comprising a plurality of the storage tubes 440 linked together in a nest 352 near the proximal ends 444 thereof. The tray 350 may include a handle storage tube 380 attached to the tray 350, with the handle storage tube 380 having a handle cavity 382 for accepting the handle assembly 20. The handle storage tube 380 may include a handle storage tube snap 384, and the flexible arm 64 of the outer surface 61 of the handle collar 60 may include an exterior snap 66a for engaging the handle storage tube snap 384 of the handle storage tube 380 to secure the handle assembly 20 in the handle storage tube 380.

As an alternative to the tray 350, the injection system may include a storage tube 440 apart from any tray and having a cap 414 (the exterior surface of the cap 414 is shown in phantom in FIG. 7D) for attachment to the distal end of the storage tube 440. A cylindrical outer shell (not shown) may be provided for the storage tube, with the length thereof elected to accommodate both the storage tube and the removable needle shield 280 in a manner comparable to nest 352 and shell 358 of the tray 350. The cap 414 may connect to the storage tube 440 in the same manner as the above-described needle shield puller 300 attaches to the tray 350 and may engage the lower housing assembly 160 in the same manner. The cap 414 (an exemplary shape thereof appears in phantom in FIG. 7D) may have arms 306 and a locking tooth 308 as described with respect to the needle shield puller 300.

The injection system 10 may include a visual indicator of the progress of an injection. The visual indicator may comprise an opening in the side wall of the syringe housing 180 and a colored body configured to advance distally while being visible to a person viewing the injection system during injection. The visual indicator may comprise one or more of a portion of the plunger 52, and may comprise a visually distinct portion of the syringe sleeve 210, the visually distinct portion being visible through the visual indicator opening only when the syringe sleeve 210 is extended distally beyond the second position. The visual indicator also may comprise a distal segment 232 of the syringe sleeve 210 being molded from a different color polymer material from the adjacent portion 234.

Operation of the injection system 10 will now be described with reference to the embodiment shown in the FIGS. 1-20B. A manufacturer or assembler may assemble an injection system 10 according to the disclosure by installing the syringe 270 into the syringe housing assembly 160. The syringe 270 is preferably pre-filled and is preferably equipped with the needle shield 280 installed on the distal end 274. The syringe 270 is installed by advancing the syringe 270 distally into the syringe housing 180 through the proximal opening into the interior 188. The syringe sleeve 210 is a component of the syringe housing assembly 160 and is installed therein, configured as described above. The syringe housing assembly 160 may be passed into one of the storage tubes 440 through the opening 452 in the proximal end 444 thereof and advanced distally until the syringe housing assembly 160 is engaged with and supported by the syringe housing assembly landing 454. The storage tube 440 has external alignment features, for example, one or more tabs or recesses, such as guiding recesses 462, or may have an eccentric shape or feature of one or more of the cavity 450 and the syringe housing assembly 160, so that the syringe housing assembly 160 is secured in a selected orientation, or in one of two selected orientations, with respect to the storage tube body 442. On a distally facing distal surface 458 of the storage tube body 442 is an interlocking mechanism for slidably accepting a needle shield puller 300 in a first orientation. The interlocking mechanism comprises a set of distal arms 459 with projecting tabs 460 and distal legs 447, each having a radially inwardly locking projection 464. The distal arms 459 and distal legs 447 are configured and arranged to accommodate the needle shield puller 300 being inserted axially between the projecting tabs 460 and the distal legs 447 in the first orientation, so that when the needle shield puller 300 is rotated to a second orientation, preferably differing from the first orientation by about ninety degrees of rotation, the projecting tabs 460 engage the base plate 310, providing distal support, and the locking projections 464 of the distal legs 447 engage the locking notches 312 of the needle shield puller 300 to secure the needle shield puller 300 to the storage tube body 442, while rotating the arms 306 of the needle shield puller 300 to engage the needle shield 280 as described herein. The needle shield puller 300 has an arm 306 extending distally into the opening 452 of the syringe tube 440, and the arm 306 and the syringe housing assembly 160 are oriented so that when the needle shield puller 300 is inserted proximally into the distal end 446 of the syringe tube 440 and passes through the opening 215 in the distal end 214 of the syringe sleeve, the arm 306 is aligned with a window 230 of the syringe sleeve 210, so that the arm 306 is free to flex radially outwardly as the flange 282 of the needle shield 300 passes the tooth 308 of the arm 306. The needle shield puller 300 or the syringe housing assembly 160 may be inserted into the syringe tube 440 together, and the order in which the two components may be inserted is preferably reversible. Once the needle shield puller 300 and the syringe housing assembly 160 both have been inserted into the syringe tube 440, the needle shield puller 300 may be rotated to the second position, in which the needle shield puller 300 is secured to the storage tube 440 and the arm 306 is at least partially unaligned with the window 230 of the syringe sleeve 210. In the second position, the outer surface 218 of the syringe sleeve 210 supports the arm 306 against a radially inward flexing movement by the outer surface 218 of the syringe sleeve 210, and the arm 306 does not flex sufficiently to accommodate the passage of the flange 282 of the needle shield. As a result, the needle shield puller 300 is secured to the needle shield 280, so that when the syringe housing assembly 160 is removed from the storage tube 440 through the opening 252, the needle shield 280 is removed from the syringe 270, readying the syringe for an injection.

The user may remove the handle assembly 20 from the handle storage tube 380 by pulling the handle assembly 20 proximally with sufficient force that radially inwardly sloped surface of the snap 59 interacting with the handle storage tube snap 384 cams the arm 64 of the handle assembly 20 radially inwardly, allowing the handle storage tube snap 384 to release the handle assembly 20. Naturally, in embodiments where the handle assembly 20 does not have a designated storage container, this step may be disregarded.

The user may remove a foil cover 356 from an appropriate storage tube 440 containing an unused syringe housing assembly 160. Preferably, the opening 452 of the storage tube 440 is shaped such that the handle assembly 40 can only be received in an orientation which will allow the proper interlocking of the handle assembly 40 to the syringe housing assembly 160. For example, the handle collar 60 may have radially outwardly extending guiding tabs 70 that align with corresponding guiding recesses 462 (FIG. 5) in the opening 452 to allow the handle collar 60 to enter the storage tube 440 in a selected orientation.

As the handle collar 60 moves distally within the cavity 450 of the storage tube 440, the handle collar 60 will receive the proximal end of the syringe housing assembly 160 until the interior snap fitting 66b slides over the corresponding exterior snap fitting 190 of the syringe housing 180, causing the arm 64 of the handle collar 60 to flex radially outwardly. Once the external snap fitting 190 is cleared, the arm 64 snaps back to its rest position, allowing the exterior snap fitting 66a of the handle collar 66 to engage a distal edge of the exterior snap fitting 190 of the syringe housing 180. Simultaneously, the plunger 52 enters the proximal end of the syringe 270. The handle assembly 20 is now connected to the syringe housing assembly 160, which is ready for removal from the storage tube 440.

The user may pull the handle assembly 20 proximally, whereupon the needle shield puller 300 acts to hold the needle shield 280 of the syringe 270 in place while the syringe housing assembly 160 and syringe 270 are removed proximally from the storage tube 440. Preferably, the needle shield puller 300 and the removed needle shield 280 drop to the distal end of the storage tube 440 upon removal of the syringe housing assembly 160, thereby providing adequate clearance for reinsertion of the syringe housing assembly 160 following completion of injection.

The handle assembly 20 and the syringe housing assembly 160 being connected (i.e., in the second device configuration described earlier), the user may initiate an injection process. Skin contact surface 216 is placed in contact with the injection site. The user applies distal pressure to the handle body 40, which causes the syringe sleeve 210 to move proximally within the syringe housing 180 toward the second position, and the needle 276 can enter the skin. The syringe sleeve 210 proximal motion engages the distal contact surface 138 of the handle pusher 130, which causes the handle pusher 130 to move proximally with respect to the handle collar 60. The handle pusher projection 140 consequently rides in the handle barrel track 110 toward the second end 114 thereof, causing rotation of the handle barrel 100 with respect to the handle collar 60 to the second handle barrel position. As described above, this rotation moves the handle body landing 108 out of circumferential alignment with the handle body projection of the handle body 40. As the syringe sleeve 210 bottoms out in its axial motion, the handle body 40 is now free to move distally with respect to the handle collar 60 and the syringe housing assembly 160. Further distal pressure on the handle body 40 causes the plunger 52 to move distally with respect to the syringe 270, thereby expelling the medicine into the user through the needle 276. Distal motion of the handle body 40 with respect to the handle collar 60 compresses the spring 150, preferably against the handle pusher 130.

As the syringe sleeve 210 moves proximally within the syringe housing 180, the locking pin 220 of the syringe sleeve 210 moves along the cam surface 248 of the rotary collar 240, causing rotation of the rotary collar 240 with respect to the syringe housing 180 and the syringe sleeve 210. When the syringe sleeve 210 reaches the second position, the locking pin 220 releases from the cam surface 248 into circumferential alignment with the locking arm 324 of the rotary collar 240.

As the handle body 40 moves distally to cause the injection, the resilient arm 328 of the audio alert means 320 preferably rides proximally along the track 332 on the handle body 40 with relative proximal movement of the handle collar 60. Once the handle body 40 reaches the end of its distal travel (i.e., injection is complete), the resilient arm 328 clears the track 332 and the striker 322 strikes the strike plate 324, causing a clicking noise that indicates to the user that injection is complete.

Following injection, the user releases pressure on the handle body 40, allowing the spring to drive the handle body 40 back to its starting position with respect to the handle collar 60, and removes the plunger 52 from the syringe 270. This motion forces rotation of the handle barrel 100 back to its original first handle barrel position, thereby moving the handle pusher projection 140 back toward the first end 112 of the handle barrel track 110, and causing distal motion of the handle pusher 130. The handle pusher 130 imparts this distal motion to the syringe sleeve 210 with respect to the syringe housing 180. The rotary collar 240 in the syringe housing assembly 160 does not rotate post-injection, which allows the locking pin 220 of the syringe sleeve 210 to move distally along the locking arm 254. When the user moves the handle assembly 20 proximally after completing the injection, the needle 276 is pulled out of the skin, and the syringe sleeve 210 advances distally to cover the needle 276 and reduce the risk of injury. The syringe sleeve 210 moves distally beyond its first position to the third position, whereupon the locking pin 220 traverses the locking surface 258 of the locking arm 254 and is then locked in place to prevent the syringe sleeve 210 from moving proximally with respect to the syringe housing 180 again.

After removing from the injection site, the syringe housing assembly 160 can be returned to its storage tube 440. As before, the handle assembly 20 must be appropriately oriented with respect to the opening 352 to allow reinsertion of the syringe housing assembly 160. Since the syringe sleeve 210 is in the third position, as the syringe housing assembly 160 distally approaches the landing 454 in the storage tube 440, the locking flange 226 on the syringe sleeve 210 will engage the locking projections 456 and cause them to flex radially outwardly. Once the locking flange 226 passes, the locking projections 456 will snap back to their original position, and prevent proximal motion of the locking flange 226, thereby preventing removal of the syringe housing assembly 160. The force caused by the locking flange 226 and the locking projections 456 will enable the user to exert a sufficient proximal force on the handle body 40 that the exterior snap fitting 66a of the handle collar 60 can proximally traverse the exterior snap fitting 190 of the syringe housing 180, causing the arm 64 of the handle collar to again flex radially outwardly. Once the external snap fitting 190 is cleared in the proximal direction, the arm 64 snaps back to its rest position, and the syringe housing assembly 160 is released from the handle assembly 20. The handle assembly 20 may be proximally removed from the storage tube 440, leaving the syringe housing assembly 160 and the used syringe 270 locked in place.

The handle assembly 20 can then be used for another injection, or it may be replaced into the handle storage tube 380 by distally pushing the handle assembly 20 with sufficient force that radially outwardly sloped surface of the snap 59 interacting with the handle storage tube snap 384 cams the flexible storage arm 55 of the handle assembly 20 radially inwardly, allowing the handle storage tube snap 384 to lock the handle assembly 20 back in place.

The devices and components described herein may be made of polymers or other materials of sufficient strength, heat resistance, corrosion resistance, and other properties to support operation of the devices and components as described herein. Suitable materials are known in the art.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

We claim:

1. An injection system comprising:
    a handle assembly having a longitudinal axis, a proximal end, and a distal end, the handle assembly comprising:
        a handle body having a proximal end, a distal end, an outer surface surrounding a handle body interior, a handle body opening at the distal end of the handle body for accessing the handle body interior, and a plunger extending through the handle body interior and oriented parallel to the longitudinal axis,
        a handle collar telescopically received within the handle body interior through the handle body opening and movable along the longitudinal axis with respect to the handle body, the handle collar having a handle collar distal restraint limiting relative distal movement of the handle collar with respect to the handle body, and a longitudinally extending arm with a radially inwardly extending snap fitting disposed at a free end thereof, and
        a handle bias member disposed between the handle body and the handle collar along the longitudinal axis to urge the handle body in a proximal direction away from the handle collar; and
    a syringe housing assembly selectively connectable to the handle assembly and oriented to the longitudinal axis when connected to the handle assembly, the syringe housing assembly comprising:
        a syringe housing having a proximal end, a distal end, an exterior side surface surrounding a syringe housing interior configured to receive at least a portion of a syringe, the exterior side surface having a syringe housing exterior snap fitting for selectively engaging the handle collar snap fitting when the handle assembly and the syringe housing assembly are connected, and a syringe sleeve telescopically received within the syringe housing interior through a distal end of the syringe housing and axially movable with respect to the syringe housing, the syringe sleeve having a proximal end a distal end with a skin contact surface.

2. The injection system of claim 1, wherein the handle collar is rotatably fixed with respect to the handle body.

3. The injection system of claim 1, wherein the syringe sleeve has a first syringe sleeve position wherein the distal end of the syringe sleeve is axially separated from the distal end of the syringe housing by a first distance, a second syringe sleeve position wherein the distal end of the syringe sleeve is axially separated from the distal end of the syringe housing by a second distance that is smaller than the first distance, and a third syringe sleeve position wherein the distal end of the syringe sleeve is axially separated from the distal end of the syringe housing by a third distance that is larger than the first distance, the handle bias member biasing the syringe sleeve toward the third syringe sleeve position when the handle assembly is connected to the syringe housing assembly.

4. The injection system of claim 1, further comprising:
a handle barrel rotatably mounted and axially fixed with respect to the handle collar and having a generally cylindrical sidewall extending between proximal and distal ends of the handle barrel and a handle body landing extending radially from the sidewall, the handle barrel being rotatable with respect to the handle body between a first handle barrel position wherein the handle body landing is circumferentially aligned with and engages a radially extending handle body projection of the handle body to restrain a distal relative movement of the handle body with respect to the handle collar, and a second handle barrel position wherein the handle body landing is out of circumferential alignment with the handle body projection such that the handle body is free to move distally with respect to the handle collar, the handle barrel having a handle barrel track arranged on the sidewall of the handle barrel, the handle barrel track being oriented at least partially non parallel to the longitudinal axis between a first end and a second end of the handle barrel track.

5. The injection system of claim 4 further comprising:
a handle pusher having a proximal end and a distal end and a handle pusher lug at the distal end thereof, the handle pusher being telescopically received within the handle collar and rotatably fixed with respect to the handle collar, the handle pusher lug having a distal contact surface, the handle pusher having a radially extending handle pusher projection that extends into the handle barrel track and is movable between the first and second ends of the handle barrel track such that, upon a proximal relative movement of the handle pusher with respect to the handle collar, the handle barrel rotates with respect to the handle collar from the first handle barrel position to the second handle barrel position, and upon a distal relative movement of the handle pusher with respect to the handle collar, the handle barrel rotates with respect to the handle collar from the second handle barrel position to the first handle barrel position.

6. The injection system of claim 1, wherein the syringe sleeve has a locking pin extending radially outwardly from the syringe sleeve outer surface, the syringe sleeve has a radially outwardly extending syringe sleeve lug at a proximal end of the syringe sleeve, and the syringe housing has a lug landing selectively aligned with and configured to support the syringe sleeve lug.

7. The injection system of claim 1, further comprising:
a rotary collar rotatably mounted and axially fixed within the syringe housing interior, the rotary collar having a proximal end, a distal end, a generally cylindrical sidewall, and a cam surface formed in the sidewall of the rotary collar, at least a portion of the cam surface extending from a first cam end proximate the distal end of the rotary collar to a second cam end that is spaced apart proximally and circumferentially from the first cam end, the rotary collar further including a flexible locking arm extending axially toward a free end with a distally facing locking surface that is distally located from a distal surface of the rotary collar, the locking pin being in contact with the cam surface at the first cam end when the syringe sleeve is in a first syringe sleeve position such that, upon proximal movement of the syringe sleeve with respect to the syringe housing from the first syringe sleeve position to the second syringe sleeve position, the locking pin interacts with the cam surface to rotate the rotary collar with respect to the syringe housing from a first rotary collar position to a second rotary collar position wherein the locking pin ceases contact with the cam surface at the second cam end and is circumferentially aligned with the flexible locking arm and the syringe sleeve is in a second syringe sleeve position, and wherein upon subsequent distal movement of the syringe sleeve with respect to the syringe housing to a third syringe sleeve position, the locking pin moves distally with respect to the rotary collar along the flexible locking arm until the locking pin passes the locking surface of the flexible locking arm, the locking surface preventing the locking pin from moving proximally with respect to the rotary collar.

8. The injection system of claim 7 wherein the rotary collar is in the first rotary collar position when the syringe sleeve is in the first syringe sleeve position and the second rotary collar position when the syringe sleeve is in the second and third syringe sleeve positions, the rotary collar having a first proximally facing syringe sleeve contact surface, and a second proximally facing syringe sleeve contact surface, the first proximally facing syringe sleeve contact surface being in contact with a distally facing surface of the syringe sleeve lug when the rotary collar is in the first rotary collar position and the syringe sleeve is in the first syringe sleeve position to prevent distal movement of the syringe sleeve with respect to the syringe housing, and the second proximally facing syringe sleeve contact surface being in contact with the distally facing surface of the syringe sleeve lug when the rotary collar is in the second rotary collar position and the syringe sleeve is in the third syringe sleeve position to prevent distal movement of the syringe sleeve with respect to the syringe housing.

9. The injection system of claim 1, wherein the distal end of the syringe sleeve has a radially outwardly extending annular locking flange, and the injection system further comprises a storage tube comprising:
a storage tube body having a proximal end, a distal end, a side wall, a cavity accessible through an opening at the proximal end of the storage tube body for accepting the syringe housing assembly, a syringe housing assembly landing within the cavity for supporting the syringe housing assembly, and a syringe housing assembly lock positioned within the cavity such that when the syringe housing assembly is supported by the syringe housing assembly landing and the syringe sleeve is in the first syringe sleeve position, the syringe housing assembly lock does not engage the locking ring of the syringe sleeve, and when the syringe housing assembly is supported by the syringe housing assembly landing and the syringe sleeve is in the third syringe sleeve position, the syringe housing assembly lock engages the locking ring of the syringe sleeve and locks the syringe housing assembly within the storage tube, wherein a distance between the proximal end of the storage tube and the syringe housing assembly lock is sufficient that the proximal end of the syringe housing assembly is countersunk distally from the proximal end of the storage tube.

10. The injection system of claim 1, further comprising an audio alert means configured to provide an audio alert when the handle body reaches an end of injection position such that the handle body cannot move any further distally with respect to the handle collar.

11. The injection system of claim 10, wherein the audio alert means comprises a striker, a strike plate, an alert biasing member operatively connected to the striker, a striker pusher for biasing the striker with respect to the strike plate and releasing the striker to strike the strike plate upon the handle body reaching the end of injection position.

12. The injection system of claim 11, wherein the striker pusher comprises a track engaging at least one of the alert biasing member and the striker during movement of the handle body with respect to the handle collar and releasing the striker upon the handle body reaching the end of injection position, the alert biasing member is attached to the handle collar, and the striker is attached to an end portion of the alert biasing member.

13. The injection system of claim 1, further comprising a tray comprising a plurality of storage tubes.

14. The injection system of claim 13 further comprising a handle storage tube attached to the tray, the handle storage tube having a handle cavity for accepting the handle assembly, the handle storage tube including a handle storage tube snap, and the outer surface of the handle body including a flexible storage arm carrying a snap for engaging the handle storage tube snap of the handle storage tube to secure the handle assembly in the handle storage tube.

15. The injection system of claim 9, further comprising a cap for the storage tube.

16. An injection system comprising:
a handle assembly having a longitudinal axis, a proximal end, and a distal end, the handle assembly comprising:
  a handle body having a proximal end, a distal end, and a plunger extending parallel to the longitudinal axis,
  a handle collar telescopically received within the handle body and movable along the longitudinal axis with respect to the handle body, the handle collar having a longitudinally extending arm with a radially inwardly extending snap fitting disposed at a free end thereof, and
  a handle bias member disposed between the handle body and the handle collar along the longitudinal axis to urge the handle body in a proximal direction away from the handle collar; and
a syringe housing assembly selectively connectable to the handle assembly and oriented to the longitudinal axis when connected to the handle assembly, the syringe housing assembly comprising:
  a syringe housing having a proximal end, a distal end, and having a syringe housing exterior snap fitting for selectively engaging the handle collar snap fitting when the handle assembly and the syringe housing assembly are connected, the syringe housing being configured to receive and support a syringe, and
  a syringe sleeve telescopically received within the syringe housing and axially movable with respect to the syringe housing, the syringe sleeve having a proximal end, and a distal end with a skin contact surface, the syringe sleeve having a first syringe sleeve position wherein the distal end of the syringe sleeve is axially separated from the distal end of the syringe housing by a first distance, a second syringe sleeve position wherein the distal end of the syringe sleeve is axially separated from the distal end of the syringe housing by a second distance that is smaller than the first distance, and a third syringe sleeve position wherein the distal end of the syringe sleeve is axially separated from the distal end of the syringe housing by a third distance that is larger than the first distance, the handle bias member biasing the syringe sleeve toward the third syringe sleeve position when the handle assembly is connected to the syringe housing assembly,
the injection system having a first configuration wherein the handle assembly is disconnected from the syringe housing assembly and the syringe sleeve is in the first syringe sleeve position, a second configuration wherein the handle assembly is connected to the syringe housing assembly and the syringe sleeve is in the first syringe sleeve position, a third configuration wherein the handle assembly is connected to the syringe housing assembly and the syringe sleeve is in the second syringe sleeve position, a fourth configuration wherein the handle assembly is connected to the syringe housing assembly and the syringe sleeve is in the third syringe sleeve position, and a fifth configuration wherein the handle assembly is disconnected from the syringe housing assembly and the syringe sleeve is in the third syringe sleeve position.

17. An injection system comprising:
a tray having a plurality of storage tubes and a handle storage tube;
a handle assembly stored in the handle storage tube, the handle assembly having a longitudinal axis, a proximal end, and a distal end, the handle assembly comprising:
  a handle body having a proximal end, a distal end, an outer surface surrounding a handle body interior, a handle body opening at the distal end of the handle body for accessing the handle body interior, and a plunger extending through the handle body interior and oriented parallel to the longitudinal axis,
  a handle collar telescopically received within the handle body interior through the handle body opening and movable along the longitudinal axis with respect to the handle body, the handle collar having a handle collar distal restraint limiting relative distal movement of the handle collar with respect to the handle body, and a longitudinally extending arm with a radially inwardly extending snap fitting disposed at a free end thereof, and
  a handle bias member disposed between the handle body and the handle collar along the longitudinal axis to urge the handle body in a proximal direction away from the handle collar; and
a plurality of syringe housing assemblies, each syringe housing assembly being stored in a corresponding one of the plurality of storage tubes and being selectively connectable to the handle assembly and oriented to the longitudinal axis when connected to the handle assembly, each syringe housing assembly comprising:

a syringe housing having a proximal end, a distal end, an exterior side surface surrounding a syringe housing interior configured to receive at least a portion of a syringe, and the exterior side surface has a syringe housing exterior snap fitting for selectively engaging the handle collar snap fitting when the handle assembly and the syringe housing assembly are connected, and a syringe sleeve telescopically received within the syringe housing interior through a distal end of the syringe housing and axially movable with respect to the syringe housing, the syringe sleeve having a proximal end and a distal end with a skin contact surface.

18. The injection system of claim 1, wherein the syringe housing receives the plunger when the handle assembly is connected to the syringe housing assembly.

19. The injection system of claim 1, further comprising the syringe.

20. The injection system of claim 1, wherein the handle collar is tubular, the syringe sleeve is tubular, and the syringe sleeve has a generally cylindrically-shaped outer surface.

* * * * *